US006872395B2

(12) United States Patent
Kawaoka

(10) Patent No.: US 6,872,395 B2
(45) Date of Patent: Mar. 29, 2005

(54) VIRUSES COMPRISING MUTANT ION CHANNEL PROTEIN

(75) Inventor: Yoshihiro Kawaoka, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 09/834,095

(22) Filed: Apr. 12, 2001

(65) Prior Publication Data

US 2003/0194694 A1 Oct. 16, 2003

Related U.S. Application Data

(60) Provisional application No. 60/197,209, filed on Apr. 14, 2000.

(51) Int. Cl.$^7$ .................. A61K 39/145; C12N 5/10; C12N 7/01; C12N 7/02

(52) U.S. Cl. ................ 424/206.1; 424/209.1; 435/235.1; 435/239; 435/325

(58) Field of Search ............... 435/325, 235.1, 435/239; 424/206.1, 209.1

(56) References Cited

U.S. PATENT DOCUMENTS 5,994,526 A    11/1999   Meulewaeter et al.

FOREIGN PATENT DOCUMENTS

| WO | 96/10632 | 4/1996 |
| WO | 96/40955 | 12/1996 |
| WO | 00/53786 | 9/2000 |

OTHER PUBLICATIONS

Duff, K.C., et al., "The secondary structure of influenza A M2 transmembrane domain", FEBS Letters, 311 (3), pp. 256–258, (Oct. 1992).
Duff, K.C., et al., "The Transmembrane Domain of Influenza A M2 Protein Forms Amantadine–Sensitive Proton Channels in Planar Lipid Bilayers", Vilology, 190(1), pp. 485–489, (Sep. 1992).
Grambas, S., et al., "Influence of Amantadine Resistance Mutations on the pH Regulatory Function of the M2 Protein of Influenza A Viruses", Virology, 191 (2), pp. 541–549, (Dec. 1992).
Hay, A.J., et al., "The role of the M2 protein in influenza A virus infection", Proceedings of the International Conference on Options for the Control of Influenza, Courchevel, pp. 281–288, (1992).
Helenius, A., "Unpacking the Incoming Influenza Virus", Cell, 69, pp. 577–578, (May 1992).
Holsinger, L.J., et al., "Influenza A Virus M2 Ion Channel Protein: a Structure–Function Analysis", Journal of Virology, 68 (3), pp. 1551–1563, (1994).

Mena, I., et al., "Rescue of a Synthetic Choramphenicol Acetyltransferase RNA into influenza Virus–Like Particles obtained from recombinant plasmids", J. of Virology, vol. 70, No. 8, XP002150091, 5016–5024, (Aug. 1996).
Neumann, G., et al., "Generation of influenza A Viruses entirely from cloned cDNAs", Proc. of the Nat'l Aca. of Sciences, USA, vol. 96, XP002150093, 9345–9350, (Aug. 1999).
Neumann, G., et al., "Plasmid–Driven Formation of Influenza Virus–Like Particles", J. of Virology, vol. 74, No. 1, XP002150094, 547–551, (Jan. 2000).
Neumann, G., et al., "RNA Polymerase I–Mediated Expression of Influenza Viral RNA Molecules", Virology, vol. 202, No. 1, XP000952667, 477–479, (Jul. 1994).
Neirynck, S., et al., "A universal influenza A vaccine based on the extracellular domain of the M2 protein", Nature Medicine, 5 (10), pp. 1157–1163, (Oct. 1999).
Piller, S.C., et al., "Vpr protein of human immunodeficiency virus type 1 forms cation–selective channels in planar lipid bilayers", PNAS, 93, pp. 111–115, (Jan. 1996).
Pinto, L.H., et al., "Influenza Virus M2 Protein Has Ion Channel Activity", Cell, 69, pp. 517–528, (May 1992).
Pleschka, S., et al., "A Plasmid–Based Reverse Gentics System for Influenza A Virus", J. of Virology, vol. 70, No. 6, XP002150092, 4188–4192, (Jun. 1996).
Sansom, M.S., et al., "Influenza virus M2 Protein: a molecular modelling study of the ion channel", Protein Engineering, 6 (1), pp. 65–74, (1993).
Skehel, J.J., et al., "On the Mechanism of Inhibition of Influenza Virus Replication by Amantadine Hydrochloride", The Journal of General Virology, 38 (1), pp. 97–110, (1977).
Sugrue, R.J., et al., "Specific structural alteration of the influenza haemagglutinin by amantadine", The EMBO Journal, 9 (11), pp. 3469–3476, (1990).
Sugrue, R.J., et al., "Structural Characteristics of the M2 Protein of Influenza A Viruses: Evidence That It Forms a Tetrameric Channel", Virology, 180, pp. 617–624, (1991).
Takeuchi, K., et al., "Influenza Virus M2 Protein Ion Channel Activity Stabilizes the Native Form of Fowl Plague Virus Hemagglutinin during Intracellular Transport", Journal of Virology, 68 (2), pp. 911–919, (Feb. 1994).
Wang, C., et al., "Ion Channel Activity of Influenza A Virus M2 Protein: Characterization of the Amantadine Block", Journal of Virology, 67 (9), pp. 5585–5594, (Sep. 1993).
Castrucci, M.R., et al., "Reverse Genetics system for generation of an influenza A virus mutant containing a deletion of the carboxyl–Terminal residue of M2 protein", J. of Virology, vol. 69, No. 5, (May 1995), pp. 2725–2728.

(Continued)

Primary Examiner—Terry McKelvey
(74) Attorney, Agent, or Firm—Schwegman, Lundberg, Woessner & Kluth, P.A.

(57) ABSTRACT

A method to prepare viruses lacking ion channel activity is provided.

17 Claims, 13 Drawing Sheets

OTHER PUBLICATIONS

Park, E.K., et al., "The M2 Ectodomain is important for its incorporation into influenza A virions", *J. of Virology,* vol. 72, No. 3, (Mar. 1998), pp. 2449–2455.

Pekosz, A., et al., "Influenza C virus CM2 integral membrane glycoprotein is produced from a polypeptide precursor by cleavage of an internal signal sequence", *PNAS,* vol. 95, (Oct. 1998), pp. 13233–13238.

Sunstrom, N.A., et al., "Ion Channels formed by NB, an influenza B virus Protein", *J. of Membrane Biology,* vol. 150, (Dec. 1996), pp. 127–132.

Sweet, T.M., et al., "Creation of Amantadine resistant clones of influenza type A virus using a new transfection procedure", *J of Virological Methods,* vol. 69, (1997), pp. 103

PA-A1284C  PA-T846C  WSN-PR/8/34-PB1

PolI-5'WPB2 (SEQ ID NO:19)
CAC ACA CGT CTC GTA TTA GTA GAA ACA AGG TCG TTT TTA AAC TAT TCG
ACA CTA ATT GAT GGC CAT CCG AAT TCT TTT GG
Length: 80 nt   Overlap: 26 nt PolI-3'WPB2 (SEQ ID NO:20)
CAC ACA CGT CTC CGG GAG CGA AAG CAG GTC AAT TAT ATT CAA TAT GGA
AAG AAT AAA AGA ACT AAG G
Length: 67 nt   Overlap: 24 nt PolI-5'WPB1 (SEQ ID NO:21)
CAC ACA CGT CTC GTA TTA GTA GAA ACA AGG CAT TTT TTC ATG AAG GAC
AAG CTA AAT TCA CTA TTT TTG CCG TCT GAG CTC TTC AAT GG
Length: 89   Overlap: 26 nt PolI-3'WPB1 (SEQ ID NO:22)
CAC ACA CGT CTC CGG GAG CGA AAG CAG GCA AAC CAT TTG AAT GGA TGT
CAA TCC GAC TTT ACT TTT C
Length: 67 nt   Overlap 27 nt PolI-5'WPA (SEQ ID NO:23)
CCA ACC CGT CTC CTA TTA GTA GAA ACA AGG TAC TTT TTT GGA CAG TAT
GGA TAG CAA ATA GTA GCA TTG CCA CAA CTA TCT CAA TGC ATG TGT GAG
GAA GGA G
Length:103   Overlap: 25 nt PolI-3'WPA (SEQ ID NO:24)
CCA ACC CGT CTC CGG GAG CGA AAG CAG GTA CTG ATT CAA AAT GGA AGA
TTT TGT GCG ACA ATG CTT C
Length: 67 nt   Overlap: 27 nt PolI-5'WHA (SEQ ID NO:25)
CAC ACA CGT CTC CTA TTA GTA GAA ACA AGG GTG TTT TTC C
Length: 40 nt   Overlap: 22 nt PolI-3'WHA (SEQ ID NO:26)
CAC ACA CGT CTC CGG GAG CAA AAG CAG GGG AAA AT  AAA AAC AAC C
Length: 46 nt   Overlap: 29 nt

FIG. 6A

PolI-5'WNP (SEQ ID NO:27)
CAC ACA CGT CTC CTA TTA GTA GAA ACA AGG GTA TTT TTC TTT AAT TG
Length: 47 nt   Overlap: 30 nt PolI-3'WNP (SEQ ID NO:28)
CAC ACA CGT CTC CGG GAG CAA AAG CAG GGT AGA TAA TCA CTC
Length: 42 nt   Overlap: 26 nt PolI-5'WNA (SEQ ID NO:29)
CAC ACA CGT CTC CTA TTA GTA GAA ACA AGG AGT TTT TTG AAC AAA C
Length: 46 nt   Overlap: 29 nt PolI-3'WNA (SEQ ID NO:30)
CAC ACA CGT CTC CGG GAG CGA AAG CAG GAG TTT AAA TGA ATC CAA ACC
Length: 48 nt   Overlap: 32 nt PolI-5'WM (SEQ ID NO:31)
CAC ACA CGT CTC CTA TTA GTA GAA ACA AGG TAG TTT TTT ACT CCA GC
Length: 47 nt   Overlap: 30 nt PolI-3'WM (SEQ ID NO:32)
CAC ACA CGT CTC CGG GAG CAA AAG CAG GTA GAT ATT GAA AG
Length: 41 nt   Overlap: 26 nt PolI-5'WNS (SEQ ID NO:33)
CAC ACA CGT CTC CTA TTA GTA GAA ACA AGG GTG TTT TTT ATT ATT AAA TAA GC
Length: 53 nt   Overlap: 36 nt PolI-3'WNS (SEQ ID NO:34)
CAC ACA CGT CTC CGG GAG CAA AAG CAG GGT GAC AAA GAC ATA ATG G
Length: 46 nt   Overlap: 30 nt Italics:  BsmBI recognition sequence
Underlined:  Influenza virus sequence
Underlined + Bold:  Influenza virus coding region

FIG. 6B

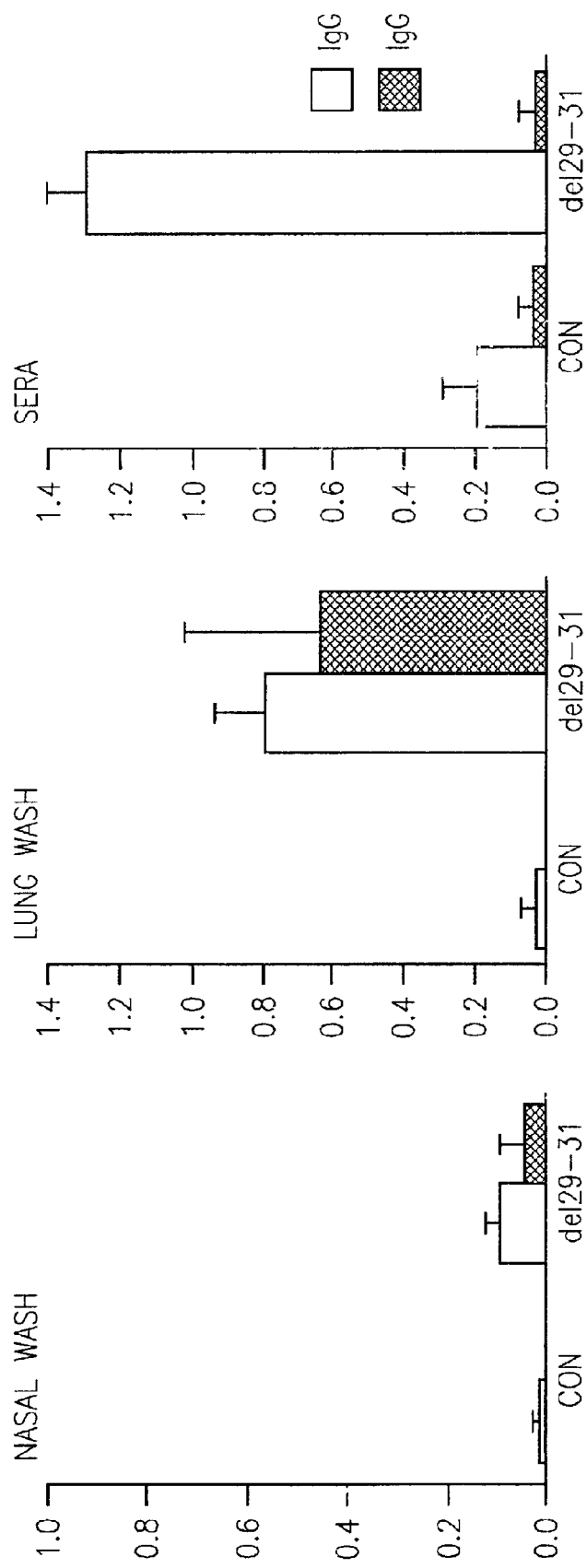

SEQUENCE LISTING

<160> NUMBER OF SEQ ID NOS: 35

<210> SEQ ID NO 1
<211> LENGTH: 19
<212> TYPE: DNA
<213> ORGANISM: Artificial Sequence
<220> FEATURE:
<223> OTHER INFORMATION: A primer

<400> SEQUENCE: 1
aagagggtca cttgaatcg                                            19

```
<210> SEQ ID NO 2
<211> LENGTH: 18
<212> TYPE: DNA
<213> ORGANISM: Artificial Sequence
<220> FEATURE:
<223> OTHER INFORMATION: A primer

<400> SEQUENCE: 2
actgttgctg cgagtatc                                                   18

<210> SEQ ID NO 3
<211> LENGTH: 18
<212> TYPE: DNA
<213> ORGANISM: Artificial Sequence
<220> FEATURE:
<223> OTHER INFORMATION: A primer

<400> SEQUENCE: 3
gttgttgctc caactatc                                                   18

<210> SEQ ID NO 4
<211> LENGTH: 18
<212> TYPE: DNA
<213> ORGANISM: Artificial Sequence
<220> FEATURE:
<223> OTHER INFORMATION: A primer

<400> SEQUENCE: 4
gttgttgctg cgaacatc                                                   18

<210> SEQ ID NO 5
<211> LENGTH: 22
<212> TYPE: DNA
<213> ORGANISM: Artificial Sequence
<220> FEATURE:
<223> OTHER INFORMATION: A primer

<400> SEQUENCE: 5
gttgttatca ttgggatctt gc                                              22

<210> SEQ ID NO 6
<211> LENGTH: 18
<212> TYPE: DNA
<213> ORGANISM: Artificial Sequence
<220> FEATURE:
<223> OTHER INFORMATION: A primer

<400> SEQUENCE: 6
cccaatgata ctcgcagc                                                   18

<210> SEQ ID NO 7
<211> LENGTH: 25
<212> TYPE: DNA
<213> ORGANISM: Artificial Sequence
<220> FEATURE:
<223> OTHER INFORMATION: A primer

<400> SEQUENCE: 7
atcttgcact tgatattggc aattc                                           25

<210> SEQ ID NO 8
<211> LENGTH: 62
<212> TYPE: DNA
<213> ORGANISM: Artificial Sequence
<220> FEATURE:
<223> OTHER INFORMATION: A primer
```

```
<400> SEQUENCE: 8
caccagtgaa ctggcgacag ttgagtagat cgccagaatg tcacttgaat cgttgcatct    60
gc                                                                   62

<210> SEQ ID NO 9
<211> LENGTH: 57
<212> TYPE: DNA
<213> ORGANISM: Artificial Sequence
<220> FEATURE:
<223> OTHER INFORMATION: A primer

<400> SEQUENCE: 9
cttttggtct ccctgggggc aatcagtttc tggatggatc gtcttttttt caaatgc       57

<210> SEQ ID NO 10
<211> LENGTH: 68
<212> TYPE: DNA
<213> ORGANISM: Artificial Sequence
<220> FEATURE:
<223> OTHER INFORMATION: A primer

<400> SEQUENCE: 10
gcttagtatc aattgtattc catttatgat tgatatccaa atgctgtcac ttgaatcgtt    60
gcatctgc                                                             68

<210> SEQ ID NO 11
<211> LENGTH: 63
<212> TYPE: DNA
<213> ORGANISM: Artificial Sequence
<220> FEATURE:
<223> OTHER INFORMATION: A primer

<400> SEQUENCE: 11
attataggag tcgtaatgtg tatctcaggg attaccataa tagatcgtct tttttcaaa     60 tgc                                                                  63

<210> SEQ ID NO 12
<211> LENGTH: 33
<212> TYPE: DNA
<213> ORGANISM: Artificial Sequence
<220> FEATURE:
<223> OTHER INFORMATION: A sequence from the pHH21 vector

<400> SEQUENCE: 12
gggttattgg agacggtacc gtctcctccc ccc                                 33

<210> SEQ ID NO 13
<211> LENGTH: 18
<212> TYPE: DNA
<213> ORGANISM: Artificial Sequence
<220> FEATURE:
<223> OTHER INFORMATION: The end of a PCR product
<221> NAME/KEY: misc_feature
<222> LOCATION: (1)...(18)
<223> OTHER INFORMATION: n = A, T, C or G

<400> SEQUENCE: 13
cgtctcntat tagtagaa                                                  18

<210> SEQ ID NO 14
<211> LENGTH: 16
<212> TYPE: DNA
<213> ORGANISM: Artificial Sequence
<220> FEATURE:
```

-continued

```
<223> OTHER INFORMATION: The end of a PCR product
<221> NAME/KEY: misc_feature
<222> LOCATION: (1)...(16)
<223> OTHER INFORMATION: n = A, T, C or G

<400> SEQUENCE: 14
ttttgctccc ngagac                                                      16

<210> SEQ ID NO 15
<211> LENGTH: 11
<212> TYPE: DNA
<213> ORGANISM: Artificial Sequence
<220> FEATURE:
<223> OTHER INFORMATION: The end of a PCR product following digestion
      with BsmBI

<400> SEQUENCE: 15
tattagtaga a                                                           11

<210> SEQ ID NO 16
<211> LENGTH: 10
<212> TYPE: DNA
<213> ORGANISM: Artificial Sequence
<220> FEATURE:
<223> OTHER INFORMATION: The end of a PCR product following digestion
      with BsmBI

<400> SEQUENCE: 16
gggagcaaaa                                                             10

<210> SEQ ID NO 17
<211> LENGTH: 15
<212> TYPE: DNA
<213> ORGANISM: Artificial Sequence
<220> FEATURE:
<223> OTHER INFORMATION: A sequence from the pHH21 vector including
      influenzal viral cDNA that was cloned into the
      vector

<400> SEQUENCE: 17
gggttattag tagaa                                                       15

<210> SEQ ID NO 18
<211> LENGTH: 13
<212> TYPE: DNA
<213> ORGANISM: Artificial Sequence
<220> FEATURE:
<223> OTHER INFORMATION: A sequence from the pHH21 vector including
      influenzal viral cDNA that was cloned into the
      vector

<400> SEQUENCE: 18
ttttgctccc ccc                                                         13

<210> SEQ ID NO 19
<211> LENGTH: 80
<212> TYPE: DNA
<213> ORGANISM: Artificial Sequence
<220> FEATURE:
<223> OTHER INFORMATION: A primer

<400> SEQUENCE: 19
cacacacgtc tcgtattagt agaaacaagg tcgttttaa actattcgac actaattgat       60
ggccatccga attcttttgg                                                  80

<210> SEQ ID NO 20
```

```
<211> LENGTH: 67
<212> TYPE: DNA
<213> ORGANISM: Artificial Sequence
<220> FEATURE:
<223> OTHER INFORMATION: A primer

<400> SEQUENCE: 20
cacacacgtc tccgggagcg aaagcaggtc aattatattc aatatggaaa gaataaaaga    60
actaagg                                                              67

<210> SEQ ID NO 21
<211> LENGTH: 89
<212> TYPE: DNA
<213> ORGANISM: Artificial Sequence
<220> FEATURE:
<223> OTHER INFORMATION: A primer

<400> SEQUENCE: 21
cacacacgtc tcgtattagt agaaacaagg catttttca tgaaggacaa gctaaattca     60 ctattttgc cgtctgagct cttcaatgg                                        89

<210> SEQ ID NO 22
<211> LENGTH: 67
<212> TYPE: DNA
<213> ORGANISM: Artificial Sequence
<220> FEATURE:
<223> OTHER INFORMATION: A primer

<400> SEQUENCE: 22
cacacacgtc tccgggagcg aaagcaggca aaccatttga atggatgtca atccgacttt    60
acttttc                                                              67

<210> SEQ ID NO 23
<211> LENGTH: 103
<212> TYPE: DNA
<213> ORGANISM: Artificial Sequence
<220> FEATURE:
<223> OTHER INFORMATION: A primer

<400> SEQUENCE: 23
ccaacccgtc tcctattagt agaaacaagg tactttttg gacagtatgg atagcaaata     60
gtagcattgc cacaactatc tcaatgcatg tgtgaggaag gag                      103

<210> SEQ ID NO 24
<211> LENGTH: 67
<212> TYPE: DNA
<213> ORGANISM: Artificial Sequence
<220> FEATURE:
<223> OTHER INFORMATION: A primer

<400> SEQUENCE: 24
ccaacccgtc tccgggagcg aaagcaggta ctgattcaaa atggaagatt ttgtgcgaca    60
atgcttc                                                              67

<210> SEQ ID NO 25
<211> LENGTH: 40
<212> TYPE: DNA
<213> ORGANISM: Artificial Sequence
<220> FEATURE:
<223> OTHER INFORMATION: A primer

<400> SEQUENCE: 25
cacacacgtc tcctattagt agaaacaagg gtgttttcc                           40
```

-continued

<210> SEQ ID NO 26
<211> LENGTH: 45
<212> TYPE: DNA
<213> ORGANISM: Artificial Sequence
<220> FEATURE:
<223> OTHER INFORMATION: A primer

<400> SEQUENCE: 26
cacacacgtc tccgggagca aaagcagggg aaaataaaaa caacc         45

<210> SEQ ID NO 27
<211> LENGTH: 47
<212> TYPE: DNA
<213> ORGANISM: Artificial Sequence
<220> FEATURE:
<223> OTHER INFORMATION: A primer

<400> SEQUENCE: 27
cacacacgtc tcctattagt agaaacaagg gtattttttct ttaattg        47

<210> SEQ ID NO 28
<211> LENGTH: 42
<212> TYPE: DNA
<213> ORGANISM: Artificial Sequence
<220> FEATURE:
<223> OTHER INFORMATION: A primer

<400> SEQUENCE: 28
cacacacgtc tccgggagca aaagcagggt agataatcac tc             42

<210> SEQ ID NO 29
<211> LENGTH: 46
<212> TYPE: DNA
<213> ORGANISM: Artificial Sequence
<220> FEATURE:
<223> OTHER INFORMATION: A primer

<400> SEQUENCE: 29
cacacacgtc tcctattagt agaaacaagg agttttttga acaaac          46

<210> SEQ ID NO 30
<211> LENGTH: 48
<212> TYPE: DNA
<213> ORGANISM: Artificial Sequence
<220> FEATURE:
<223> OTHER INFORMATION: A primer

<400> SEQUENCE: 30
cacacacgtc tccgggagcg aaagcaggag tttaaatgaa tccaaacc        48

<210> SEQ ID NO 31
<211> LENGTH: 47
<212> TYPE: DNA
<213> ORGANISM: Artificial Sequence
<220> FEATURE:
<223> OTHER INFORMATION: A primer

<400> SEQUENCE: 31
cacacacgtc tcctattagt agaaacaagg tagttttttta ctccagc         47

<210> SEQ ID NO 32
<211> LENGTH: 41
<212> TYPE: DNA
<213> ORGANISM: Artificial Sequence
<220> FEATURE:

-continued

```
<223> OTHER INFORMATION: A primer

<400> SEQUENCE: 32
cacacacgtc tccgggagca aaagcaggta gatattgaaa g                 41

<210> SEQ ID NO 33
<211> LENGTH: 53
<212> TYPE: DNA
<213> ORGANISM: Artificial Sequence
<220> FEATURE:
<223> OTHER INFORMATION: A primer

<400> SEQUENCE: 33
cacacacgtc tcctattagt agaaacaagg gtgtttttta ttattaaata agc    53

<210> SEQ ID NO 34
<211> LENGTH: 46
<212> TYPE: DNA
<213> ORGANISM: Artificial Sequence
<220> FEATURE:
<223> OTHER INFORMATION: A primer

<400> SEQUENCE: 34
cacacacgtc tccgggagca aaagcagggt gacaaagaca taatgg            46

<210> SEQ ID NO 35
<211> LENGTH: 19
<212> TYPE: PRT
<213> ORGANISM: Influenza A virus

<400> SEQUENCE: 35

Pro Leu Val Val Ala Ala Ser Ile Ile Gly Ile Leu His Leu Ile Leu
1               5                   10                  15

Trp Ile Leu
```

VIRUSES COMPRISING MUTANT ION CHANNEL PROTEIN

CROSS-REFERENCE TO RELATED APPLICATION

This application is a continuation-in-part application of U.S. application Ser. No. 60/197,209, filed on Apr. 14, 2000.

STATEMENT OF GOVERNMENT RIGHTS

This invention was made with a grant from the Government of the United States of America (grants AI-29599, AI-42774 and AI-44386 from the National Institute of Allergy and Infectious Diseases). The Government may have certain rights in the invention.

BACKGROUND OF THE INVENTION

Cell membranes consist of a double layer of lipid molecules in which various proteins are embedded. Because of its hydrophobic interior, the lipid bilayer of cell membranes serves as a barrier to the passage of most polar molecules and therefore is crucial to cell viability. To facilitate the transport of small water-soluble molecules into or out of cells or intracellular compartments, such membranes possess carrier and channel proteins. Ion channels are essential for many cellular functions, including the electrical excitability of muscle cells and electrical signaling in the nervous system (reviewed by Alberts et al., 1994). They are present not only in all animal and plant cells, as well as microorganisms, but also have been identified in viruses (Ewart et al., 1996; Piller et al., 1996; Pinto et al., 1992; Schubert et al., 1996; Sugrue et al., 1990; Sunstrom et al., 1996), where they are thought to play an important role in the viral life cycle.

The influenza A virus is an enveloped negative-strand virus with eight RNA segments encapsidated with nucleoprotein (NP) (reviewed by Lamb and Krug, 1996). Spanning the viral membrane are three proteins: hemagglutinin (HA), neuramimidase (NA), and M2. The extracellular domains (ectodomains) of HA and NA are quite variable, while the ectodomain domain of M2 is essentially invariant among influenza A viruses. The life cycle of viruses generally involves attachment to cell surface receptors, entry into the cell and uncoating of the viral nucleic acid, followed by replication of the viral genes inside the cell. After the synthesis of new copies of viral proteins and genes, these components assemble into progeny virus particles, which then exit the cell (reviewed by Roizman and Palese, 1996). Different viral proteins play a role in each of these steps. In influenza A viruses, the M2 protein which possesses ion channel activity (Pinto et al., 1992), is thought to function at an early state in the viral life cycle between host cell penetration and uncoating of viral RNA (Martin and Helenius, 1991; reviewed by Helenius, 1992; Sugrue et al., 1990). Once virions have undergone endocytosis, the virion-associated M2 ion channel, a homotetrameric helix bundle, is believed to permit protons to flow from the endosome into the virion interior to disrupt acid-labile M1 protein-ribonucleoprotein complex (RNP) interactions, thereby promoting RNP release into the cytoplasm (reviewed by Helenius, 1992). In addition, among some influenza strains whose HAs are cleaved intracellularly (e.g., A/fowl plagues/Rostock/34), the M2 ion channel is thought to raise the pH of the trans-Golgi network, preventing conformational changes in the HA due to conditions of low pH in this compartment (Hay et al., 1985; Ohuchi et al., 1994; Takeuchi and Lamb, 1994).

Evidence that the M2 protein has ion channel activity was obtained by expressing the protein in oocytes of Xenopus laevis and measuring membrane currents (Pinto et al., 1992; Wang et al., 1993; Holsinger et al., 1994). Specific changes in the M2 protein transmembrane (TM) domain altered the kinetics and ion selectivity of the channel, providing strong evidence that the M2 TM domain constitutes the pore of the ion channel (Holsinger et al., 1994). In fact, the M2 TM domain itself can function as an ion channel (Duff and Ashley, 1992). M2 protein ion channel activity is thought to be essential in the life cycle of influenza viruses, because amantadine hydrochloride, which blocks M2 ion channel activity (Hay et al., 1993), inhibits viral replication (Kato and Eggers, 1969; Skehel et al., 1978). However, a requirement for this activity in the replication of influenza A viruses has not been directly demonstrated.

Generally, influenza vaccines have been prepared from live, attenuated virus or killed virus which can grow to high titers. Live virus vaccines activate all phases of the immune system and stimulate an immune response to each of the protective antigens, which obviates difficulties in the selective destruction of protective antigens that may occur during preparation of inactivated vaccines. In addition, the immunity produced by live virus vaccines is generally more durable, more effective, and more cross-reactive than that induced by inactivated vaccines. Further, live virus vaccines are less costly to produce than inactivated virus vaccines. However, the mutations in attenuated virus are often ill-defined.

Thus, what is needed is a method to prepare recombinant attenuated influenza virus for vaccines e.g., attenuated viruses having defined mutation(s).

SUMMARY OF THE INVENTION

The invention provides an isolated and purified recombinant virus comprising a mutant ion channel protein which lacks or has reduced ion channel activity relative to the activity of a corresponding wild-type ion channel protein. The activity of an ion channel protein may be measured by methods well-known to the art, see, e.g., Holsinger et al. (1994). The recombinant viruses of the invention replicate in vitro but are attenuated in vivo. Preferably, the virus is a recombinant orthomyxovirus, e.g., a recombinant influenza virus, or a recombinant lentivirus, e.g., human immunodeficiency virus (HIV). Also preferably, the mutant ion channel protein is a mutant viral ion channel protein. In one embodiment of the invention, the mutant ion channel protein comprises at least one amino acid substitution relative to the corresponding wild-type ion channel protein. The substitution(s) in the ion channel protein may be positioned in the ectodomain, the TM domain, or the cytoplasmic domain, or any combination thereof. Preferred substitutions are in or near the TM domain of the ion channel protein. For example, for influenza A virus, substitutions may be at residues 25–43 of M2, i.e., the TM domain, and preferably are at positions 27, 30, 31, 34, 38, and/or 41 of the TM domain of M2. In another embodiment of the invention, the mutant ion channel protein comprises a deletion in at least a portion of the ectodomain, the TM domain, the cytoplasmic domain, or any combination thereof. Preferably, the deletion is in or near the TM. In yet another embodiment of the invention, the mutant ion channel protein is a chimeric protein comprising a portion of an ion channel protein, e.g., the ectodomain and/or the cytoplasmic domain of a viral ion channel protein, and a heterologous protein, e.g., the TM domain of a heterologous protein. Also within the scope of the invention is a recombinant virus comprising a mutant ion channel protein comprising at least one amino acid substitution, a deletion, an insertion, a functional portion of a heterologous protein, e.g., a portion which provides a structure such as a TM domain or has a similar activity as the corresponding portion in the full length heterologous protein such as catalytic activity, binding to a ligand, or other has a detectable phenotype, or any combination thereof.

As described hereinbelow, recombinant influenza A viruses with defective M2 ion channel activity were prepared using a reverse-genetics system (see Example 1 and Neumann et al., 1999). Unexpectedly, all of the M2 ion channel mutants replicated as efficiently as the wild-type virus in vitro, although their growth was attenuated in mice. Recombinant viruses were also prepared which comprise a mutant M2 ion channel protein which is a chimeric protein, e.g., a chimeric protein in which the TM domain of M2 was replaced with the TM domain from HA or NA. These recombinant viruses replicated well in tissue culture, but were highly attenuated in mice. Thus, M2 ion channel activity is not essential for the life cycle of influenza A viruses. Rather, it may serve an auxiliary function that could, for example, promote viral replication in vivo. Given that the administration of *E. coli*-derived particles, spontaneously formed from a fusion protein containing the M2 ectodomain and a portion of the hepatitis B core protein, to mice resulted in 90–100% protection against lethal virus challenge (Neirynck et al., 1999), and that cold-adapted live vaccines are efficacious in humans, the attenuated growth of mutant M2 ion channel viruses in vivo, but not in vitro, indicates that these mutant viruses may be useful in the development of live influenza vaccines. Thus, the invention further provides a vaccine or immunogenic composition comprising the recombinant virus of the invention, and a method of using the vaccine or immunogenic composition to immunize a vertebrate or induce an immune response in a vertebrate, respectively.

Also provided is a method of preparing a recombinant influenza virus comprising a mutant ion channel protein which lacks or has reduced activity relative to the corresponding wild-type ion channel protein. The method comprises contacting a host cell with a composition comprising a plurality of influenza vectors, including a vector comprising a mutant ion channel protein, so as to yield recombinant virus. For example, for influenza A, the composition comprises: a) at least two vectors selected from a vector comprising a promoter operably linked to an influenza virus PA cDNA linked to a transcription termination sequence, a vector comprising a promoter operably linked to an influenza virus PB1 cDNA linked to a transcription termination sequence, a vector comprising a promoter operably linked to an influenza virus PB2 cDNA linked to a transcription termination sequence, a vector comprising a promoter operably linked to an influenza virus HA cDNA linked to a transcription termination sequence, a vector comprising promoter operably linked to an influenza virus NP cDNA linked to a transcription termination sequence, a vector comprising a promoter operably linked to an influenza virus NA cDNA linked to a transcription termination sequence, a vector comprising a promoter operably linked to an influenza virus M cDNA linked to a transcription termination sequence, and a vector comprising a promoter operably linked to an influenza virus NS cDNA linked to a transcription termination sequence, wherein the M cDNA comprises mutant ion channel protein DNA; and b) at least two vectors selected from a vector comprising a promoter operably linked to a DNA segment encoding influenza virus PA, a vector comprising a promoter operably linked to a DNA segment encoding influenza virus PB1, a vector comprising a promoter operably linked to a DNA segment encoding influenza virus PB2, a vector comprising a promoter operably linked to a DNA segment encoding influenza virus NP, a vector comprising a promoter operably linked to a DNA segment encoding influenza virus HA, a vector comprising a promoter operably linked to a DNA segment encoding influenza virus NA, a vector comprising a promoter operably linked to a DNA segment encoding influenza virus M1, a vector comprising a promoter operably linked to a DNA segment encoding an ion channel protein, preferably a mutant ion channel protein, and a vector comprising a promoter operably linked to a DNA segment encoding influenza virus NS2. Preferably, the mutant ion channel protein in the vector of a) or b) is a mutant M2 ion channel protein, e.g., one having at least one amino acid substitution, deletion, insertion, or heterologous sequence, which lacks or has reduced ion channel activity relative to the activity of a corresponding wild-type M2 ion channel protein. The invention further provides a composition such as that described hereinabove, and a host cell contacted with such a composition e.g., so as to yield infectious virus. Alternatively, the host cell may be contacted with each vector, or a subset of vectors, sequentially.

The invention also provides a vector encoding a chimeric protein comprising the ectodomain of an influenza virus ion channel protein linked to a heterologous transmembrane protein, preferably linked to a cytoplasmic domain, e.g., from an influenza protein which has a transmembrane domain.

BRIEF DESCRIPTION OF THE FIGURES

FIG. 5. Recovery of PA mutants. The PA gene of each virus was amplified by RT-PCR with primers that yield a 1226 bp fragment (position 677 to 1903 of the mRNA, lanes 1, 3, 5), which was then digested with the restriction enzyme Bsp120I (at position 846 of the mRNA, lanes 4, 7) or PvuII (at position 1284 of the mRNA, lanes 2, 6). The presence of Bsp120I or PvuII sites in the PCR products yielded either 169 bp and 1057 bp or 607 bp and 619 bp fragments, respectively. MW=molecular weight markers.

FIGS. 6A–6B. Primers employed to amplify influenza sequences.

FIG. 12. Virus-specific antibodies in nasal wash (A), lung wash (B) or sera (C) from vaccinated mice. Mice were intranasally immunized with 50 μl of $1.1\times10^5$ PFU/ml of M2del29-31 or wild-type WSN-UdM (control) viruses. In the second week after immunization, four mice were sacrificed to obtain samples.

DETAILED DESCRIPTION OF THE INVENTION

Definitions

Figure 1:
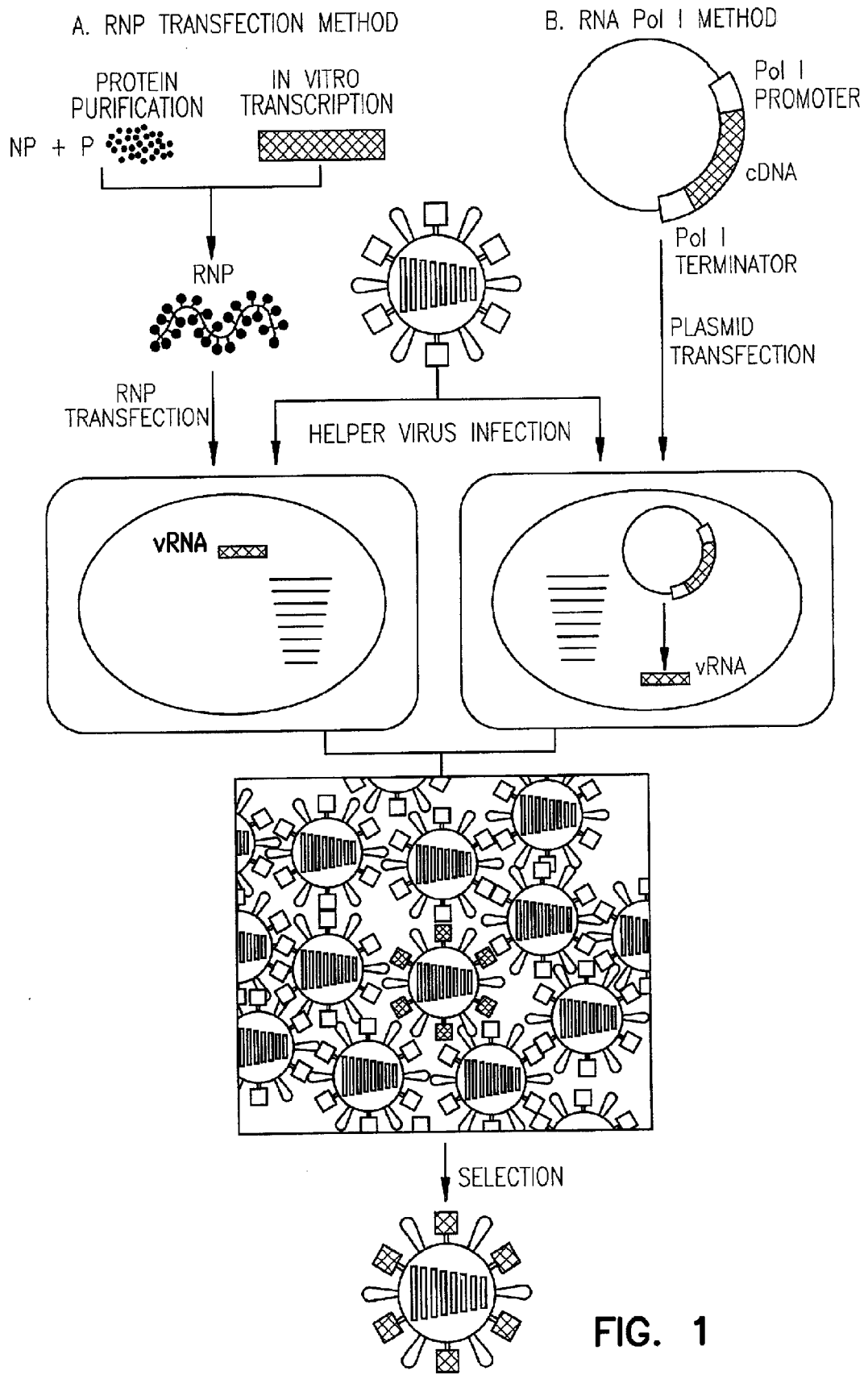
FIG. 1. Schematic diagram of established reverse genetics systems. In the RNP transfection method (A), purified NP and polymerase proteins are assembled into RNPs with use of in vitro-synthesized vRNA. Cells are transfected with RNPs, followed by helper virus infection. In the RNA polymerase I method (B), a plasmid containing the RNA polymerase I promoter, a cDNA encoding the vRNA to be rescued, and the RNA polymerase I terminator is transfected into cells. Intracellular transcription by RNA polymerase I yields synthetic vRNA, which is packaged into progeny virus particles upon infection with helper virus. With both methods, transfectant viruses (i.e., those containing RNA derived from cloned cDNA), are selected from the helper virus population.

As used herein, the terms "isolated and/or purified" refer to in vitro preparation, isolation and/or purification of a vector, plasmid or virus of the invention, so that it is not associated with in vivo substances, or is substantially purified from in vitro substances. An isolated virus preparation of the invention is generally obtained by in vitro culture and propagation and is substantially free from other infectious agents. As used herein, "substantially free" means below the level of detection for a particular infectious agent using standard detection methods for that agent. A "recombinant" virus is one which has been manipulated in vitro, e.g., using recombinant DNA techniques to introduce changes to the viral genome.

As used herein, the term "recombinant nucleic acid" or "recombinant DNA sequence or segment" refers to a nucleic acid, e.g., to DNA, that has been derived or isolated from a source, that may be subsequently chemically altered in vitro, so that its sequence is not naturally occurring, or corresponds to naturally occurring sequences that are not positioned as they would be positioned in the native genome. An example of DNA "derived" from a source, would be a DNA sequence that is identified as a useful fragment, and which is then chemically synthesized in essentially pure form. An example of such DNA "isolated" from a source would be a useful DNA sequence that is excised or removed from said source by chemical means, e.g., by the use of restriction endonucleases, so that it can be further manipulated, e.g., amplified, for use in the invention, by the methodology of genetic engineering.

Orthomyxoviruses

Influenza Virus A

Influenza A viruses possess a genome of eight single-stranded negative-sense viral RNAs (vRNAs) that encode a total of ten proteins. The influenza virus life cycle begins with binding of the HA to sialic acid-containing receptors on the surface of the host cell, followed by receptor-mediated endocytosis. The low pH in late endosomes triggers a conformational shift in the HA, thereby exposing the N-terminus of the HA2 subunit (the so-called fusion peptide). The fusion peptide initiates the fusion of the viral and endosomal membrane, and the matrix protein (M1) and RNP complexes are released into the cytoplasm. RNPs consist of the nucleoprotein (NP), which encapsidates vRNA, and the viral polymerase complex, which is formed by the PA, PB1, and PB2 proteins. RNPs are transported into the nucleus, where transcription and replication take place. The RNA polymerase complex catalyzes three different reactions: synthesis of an mRNA with a 5' cap and 3' polyA structure, of a full-length complementary RNA (cRNA), and of genomic vRNA using the cDNA as a template. Newly synthesized vRNAs, NP, and polymerase proteins are then assembled into RNPs, exported from the nucleus, and transported to the plasma membrane, where budding of progeny virus particles occurs. The neuramimidase (NA) protein plays a crucial role late in infection by removing sialic acid from sialyloligosaccharides, thus releasing newly assembled virions from the cell surface and preventing the self aggregation of virus particles. Although virus assembly involves protein-protein and protein-vRNA interactions, the nature of these interactions is largely unknown.

Although influenza B and C viruses are structurally and functionally similar to influenza A virus, there are some differences. For example, influenza B virus does not have a M2 protein with ion channel activity. Instead, the NB protein, a product of the NA gene, likely has ion channel activity and thus a similar function to the influenza A virus M2 protein. Similarly, influenza C virus does not have a M2 protein with ion channel activity. However, the CM1 protein is likely to have this activity.

Thogotovirus

Thogotoviruses (THOV) represent a new genus in the family of Orthomyxoviridae. They are transmitted by ticks and have been found in domestic animals, including camels, goats, and cattle. Consequently, THOV can replicate in tick and vertebrate cells. The THOV genome comprises six segments of single-stranded, negative-sense RNA. The proteins encoded by the three largest segments show significant homology to the influenza virus polymerase proteins PB2, PB1, and PA. Segment 5 encodes a protein related to influenza virus NP. The THOV glycoprotein, which is encoded by segment 4, is not homologous to either influenza virus HA or NA, but it shows sequence similarity to the Baculovirus glycoprotein. The smallest segment is thought to encode a matrix protein and does not resemble any of the influenza virus proteins. Like influenza virus, both the 3' and 5' ends of the vRNA are required for promoter activity, and this activity is located in the terminal 14 and 15 nucleotides of the 3' and 5' ends of the vRNA, respectively.

The mRNA synthesis of THOV is primed by host cell-derived cap structures. However, in contrast to influenza virus, only the cap structures (without additional nucleotides) are cleaved from cellular mRNAs (Albo et al., 1996; Leahy et al., 1997; Weber et al., 1996). In vitro cleavage assays revealed that both the 5' and 3' ends of vRNA are required for endonuclease activity (Leahy et al., 1998), but addition of a model cRNA promoter does not stimulate endonuclease activity (Leahy et al., 1998), as has been shown for influenza virus (Cianci et al., 1995; Hagen et al., 1994). A 'hook' structure has been proposed for THOV (Leahy et al., 1997; Weber et al., 1997), which is similar to the corkscrew structure proposed for influenza virus (Flick et al., 1996). This 'hook' structure, however, is only found in the THOV vRNA promoter. The cRNA promoter sequence does not allow the formation of base pairs between positions 2 and 9, and between 3 and 8 at the 5' end of the cRNA. Alterations at positions 3 or 8 to allow base-pairing between these nucleotides stimulates endonuclease activity, which is strong supporting evidence of the proposed 'hook' structure (Leahy et al., 1998). Moreover, this structure might be crucial for the regulation of the THOV life cycle; the vRNA promoter, forming the 'hook' structure, may stimulate PB2 endonuclease activity, thereby allowing transcription. The cRNA promoter, in contrast, may not form the 'hook' structure and may therefore be unable to stimulate endonuclease activity, thus resulting in replication.

Bunyaviridae

The family Bunyaviridae includes several viruses that cause hemorrhagic or encephalitic fevers in humans (e.g., Rift fever valley, Hantaan, La Crosse, and Crimean-Congo hemorrhagic fever). The spherical and enveloped virions contain three segments of single-stranded, negative-sense RNA (reviewed in Elliott, 1997). The largest segment (L) encodes the viral RNA polymerase protein (L protein), whereas the M segment encodes the two viral glycoproteins G1 and G2, and a nonstructural protein (NSm). The smallest segment (S) encodes the nucleocapsid protein (N) and a second nonstructural protein (NSs). Virus replication and transcription take place in the cytoplasm, and newly assembled virions bud through the membranes of the Golgi apparatus.

Bridgen & Elliott (1996) have established a reverse genetics system to generate infectious Bunyamwera virus entirely from cloned cDNAs. They followed a strategy first described by Schnell et al. (1994) for rabies virus: intracellular transcription of a cDNA coding for the positive-sense antigenomic RNA (but not for the negative-sense genomic RNA) in cells expressing the viral polymerase and nucleoprotein. Bridgen & Elliott (1996) infected HeLaT4+cells with vaccinia virus expressing T7 polymerase and transfected these cells with plasmids expressing proteins encoded by the S, M, and L segments. They then transfected these cells with three plasmids encoding full-length anti-genomic cDNAs flanked by the T7 polymerase promoter and the hepatitis delta virus ribozyme. To increase the number of bunyavirus particles relative to the number of vaccinia virus particles, the authors used mosquito cells in which Bunyamwera but not Vaccinia virus replicates. This protocol can be used not only to genetically engineer Bunyaviridae, but also generate reassortant viruses that cannot easily be obtained by coinfecting cells with different Bunyaviridae strains.

To study bunyavirus promoter elements and the viral proteins that are required for transcription and replication, Dunn et al. (1995) cloned the CAT gene in the negative-sense orientation between the 5' and 3' nontranslated regions of the Bunyamwera S RNA segment. Cells were transfected with constructs expressing the proteins encoded by the L and S segment and were then transfected with in vitro transcribed RNA, which resulted in CAT activity. The bunyavirus S segment encodes two proteins, N and NSs, in overlapping reading frames. To determine whether both of these proteins are required for transcription and replication, constructs expressing only N or NSs were tested for CAT activity. N protein expression, together with L protein, resulted in CAT activity, whereas no CAT activity was detected with the NSs expression construct. Thus, the L and N proteins are sufficient for transcription and replication of a bunyavirus-like RNA.

As with influenza virus, the terminal sequences of bunyavirus RNAs are complementary and highly conserved. It has therefore been assumed that these sequence elements define the bunyaviral promoter and are crucial for promoter activity. Deletion of five nucleotides at the 3' end of the viral RNA drastically reduces CAT expression (Dunn et al., 1995). In contrast, addition of two nucleotides at the 5' end, or of 11 or 35 nucleotides at the 3' end does not abolish CAT expression (Dunn et al., 1995). Therefore, like the influenza virus polymerase complex, the bunyavirus polymerase protein can apparently start transcription and/or replication internally.

The invention will be further described by the following non-limiting examples.

EXAMPLE 1

Material and Method

Cells and viruses. 293T human embryonic kidney cells and Madin-Darby canine kidney cells (MDCK) were maintained in Dulbecco's modified Eagle medium (DMEM) supplemented with 10% fetal calf serum and in modified Eagle's medium (MEM) containing 5% newborn calf serum, respectively. All cells were maintained at 37° C. in 5% $CO_2$. Influenza viruses A/WSN/33 (H1N1) and A/PR/8/34 (H1N1) were propagated in 10 day-old eggs.

Figure 2:
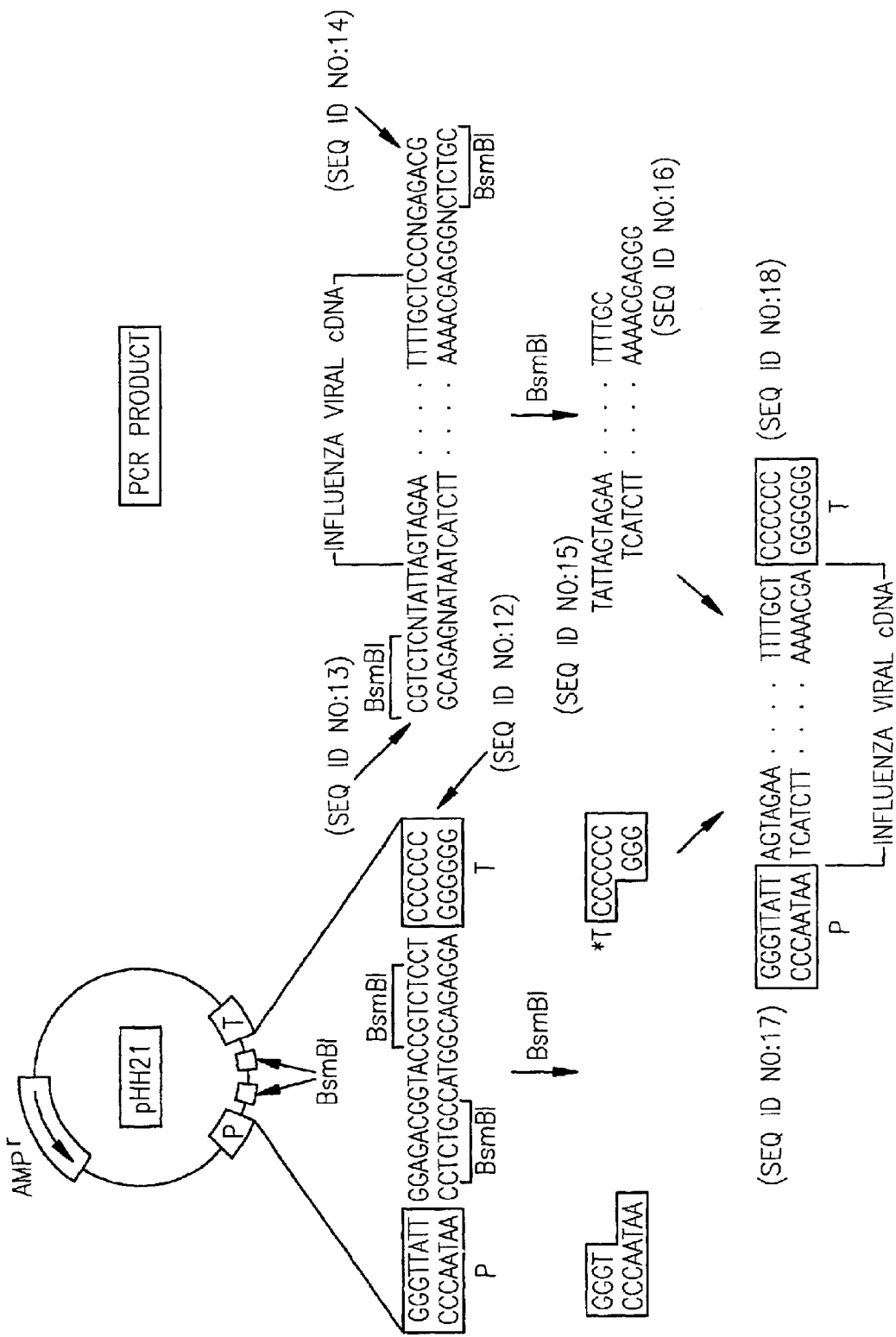
FIG. 2. Schematic diagram of the generation of RNA polymerase I constructs. cDNAs derived from influenza virus were amplified by PCR, digested with BsmBI and cloned into the BsmBI sites of the pHH21 vector (E. Hoffmann, Ph.D. thesis, Justus, Liebig-University, Giessen, Germany), which contains the human RNA polymerase I promoter (P) and the mouse RNA polymerase I terminator (T). The thymidine nucleotide upstream of the terminator sequence (*T) represents the 3' end of the influenza viral RNA. Influenza A virus sequences are shown in bold face letters.

Construction of plasmids. To generate RNA polymerase I constructs, cloned cDNAs derived from A/WSN/33 or A/PR/8/34 viral RNA were introduced between the promoter and terminator sequences of RNA polymerase I. Briefly, the cloned cDNAs were amplified by PCR with primers containing BsmBI sites, digested with BsmBI, and cloned into the BsmBI sites of the pHH21 vector which contains the human RNA polymerase I promoter and the mouse RNA polymerase I terminator, separated by BsmBI sites (FIG. 2). The PB2, PB 1, PA, HA, NP, NA, M, and NS genes of the A/WSN/33 strain were PCR-amplified by use of the following plasmids: pSCWPB2, pGW-PB1, and pSCWPA (all obtained from Dr. Debi Nayak at the University of California Los Angeles), and pWH17, pWNP152, pT3WNA15 (Castrucci et al., 1992), pGT3WM, and pWNS1, respectively. The PB1 gene of influenza A/PR18/34 virus was amplified by using pcDNA774 (PB 1) (Perez et al., 1998) as a template. See FIG. 6 for the sequences of the primers. To ensure that the genes were free of unwanted mutations, PCR-derived fragments were sequences with an autosequencer (Applied Biosystem Inc., CA, USA) according to the protocol recommended by the manufacturer. The cDNAs encoding the HA, NP, NA, and M1 genes of A/WSN/33 virus were cloned as described (Huddleston et al., 1982) and subcloned into the eukaryotic expression vector pCAGGS/MCS (controlled by the chicken β-actin promoter) (Niwa et al., 1991), resulting in pEWSN-HA, pCAGGS-WSN-NP0-14, pCAGGS-WNA15, and pCAGGS-WSN-M1-2/1, respectively. The M2 and NS2 genes from the A/PR/8/34 virus were amplified by PCR and cloned into pCAGGS/MCS, yielding pEP24c and pCA-NS2. Finally, pcDNA774 (PB 1), pcDNA762(PB2), and pcDNA787(PA) were used to express the PB2, PB 1, and PA proteins under control of the cytomegalovirus promoter (Perez et al., 1998).

Generation of infections influenza particles. 293T cells ($1 \times 10^6$) were transfected with a maximum of 17 plasmids in different amounts with use of Trans IT LT-1 (Panvera, Madison, Wis.) according to the manufacturer's instructions. Briefly, DNA and transfection reagent were mixed (2 µl Trans IT-LT-1 per µg of DNA), incubated at room temperature for 45 minutes and added to the cells. Six hours later, the DNA-transfection reagent mixture was replaced by Opti-MEM (Gibco/BRL, Gaithersburg, Md.) containing 0.3% bovine serum albumin and 0.01% fetal calf serum. At different times after transfection, viruses were harvested from the supernatant and titrated on MDCK cells. Since helper virus was not required by this procedure, the recovered transfectant viruses were analyzed without plaque purification.

Determination of the percentage of plasmid-transfected cells producing viruses. Twenty-four hours after transfection, 293T cells were dispersed with 0.02% EDTA into single cells. The cell suspension was then diluted 10-fold and transferred to confluent monolayers of MDCK cells in 24-well plates. Viruses were detected by the hemagglutination assay.

Immunostaining assay. Nine hours after infection with influenza virus, cells were washed twice with phosphate-buffered saline (PBS) and fixed with 3.7% paraformaldehyde (in PBS) for 20 minutes at room temperature. Next, they were treated with 0.1% Triton X-100 and processed as described by Neumann et al. (1997).

Results

Figure 3:
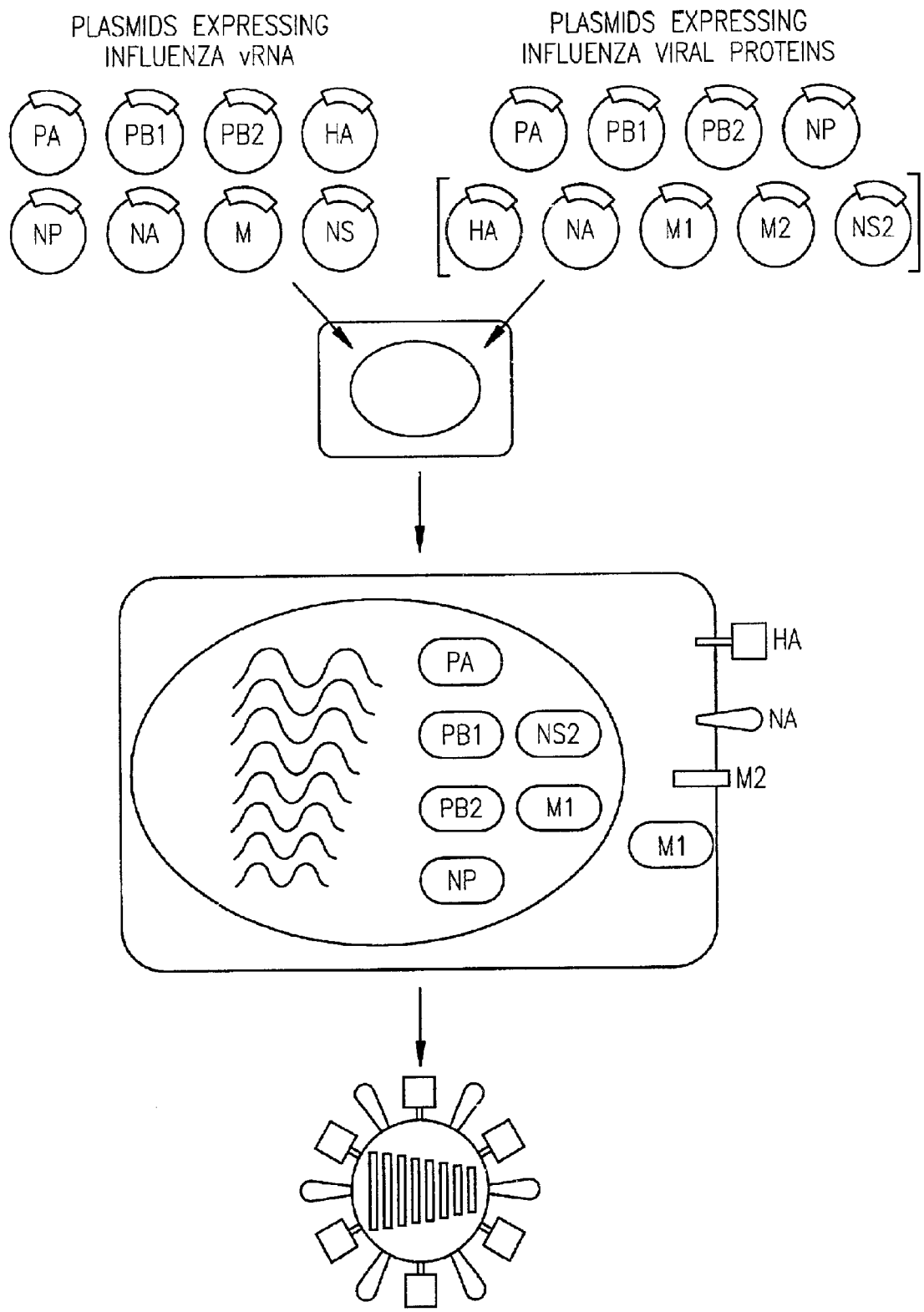
FIG. 3. Proposed reverse genetics method for generating segmented negative-sense RNA viruses. Plasmids containing the RNA polymerase I promoter a cDNA for each of the eight viral RNA segments, and the RNA polymerase I terminator are transfected into cells together with protein expression plasmids. Although infectious viruses can be generated with plasmids expressing PA, PB1, PB2, and NP, expression of all remaining structural proteins (shown in brackets) increases the efficiency of virus production depending on the virus generated.

Generation of infectious virus by plasmid-driven expression of viral RNA segments, three polymerase subunits and NP protein. Although transfection of cells with a mixture of RNPs extracted from purified virions results in infectious influenza particles, this strategy is not likely to be efficient when used with eight different in vitro generated RNPs. To produce infectious influenza viruses entirely from cDNAs, eight viral RNPs were generated in vivo. Thus, plasmids were prepared that contain cDNAs for the full-length viral RNAs of the A/WSN/33 virus, flanked by the human RNA polymerase I promoter and the mouse RNA polymerase I terminator. In principle, transfection of these eight plasmids into eukaryotic cells should result in the synthesis of all eight influenza vRNAs. The PB2, PB1, PA and NP proteins, generated by cotransfection of protein expression plasmids, should then assemble the vRNAs into functional vRNPs that are replicated and transcribed, ultimately forming infectious influenza viruses (FIG. 3). $1 \times 10^6$ 293T cells were transfected with protein expression plasmids (1 µg of pcDNA762 (PB2), 1 µg of pcDNA774(PB1), 0.1 µg of pcDNA787(PA), and 1 µg of pCAGGS-WSN-NP0/14) and 1 µg of each of the following RNA polymerase I plasmids (pPolI-WSN-PB2, pPolI-WSN-PB1, pPolI-WSN-PA, pPolI-WSN-HA, pPolI-WSN-NP, pPolI-WSN-NA, pPolI-WSN-M, and pPolI-WSN-NS). The decision to use a reduced amount of pcDNA787(PA) was based on previous observations (Mena et al., 1996), and data on the optimal conditions for generation of virus-like particles (VLPs) (data not shown). Twenty-four hours after transfection of 293T cells, $7 \times 10^3$ pfu of virus per ml was found in the supernatant (Experiment 1, Table 1), demonstrating for the first time the capacity of reverse genetics to produce influenza A virus entirely from plasmids.

TABLE 1

Plasmid sets used to produce influenza virus from cloned cDNA*

| | Experiment | | | | | | | |
|---|---|---|---|---|---|---|---|---|
| | 1 | 2 | 3 | 4 | 5 | 6 | 7 | 8 |
| RNA polymerase I plasmids for:† | | | | | | | | |
| PB1 | + | + | − | − | − | − | − | − |
| PR8-PB1 | − | − | + | + | + | + | + | + |
| PB2 | + | + | + | + | + | + | + | + |
| PA | + | + | + | + | + | + | + | + |
| HA | + | + | + | + | + | + | + | + |
| NP | + | + | + | + | + | + | + | + |
| NA | + | + | + | + | + | + | + | + |
| M | + | + | + | + | + | + | + | + |
| NS | + | + | + | + | + | + | + | + |
| Protein expression plasmids for: | | | | | | | | |
| PB1 | + | + | + | + | − | + | + | + |
| PB2 | + | + | + | + | + | − | + | + |
| PA | + | + | + | + | + | + | − | + |
| NP | + | + | + | + | + | + | + | − |
| HA | − | + | − | + | + | + | + | + |
| NA | − | + | − | + | + | + | + | + |
| M1 | − | + | − | + | + | + | + | + |
| M2 | − | + | − | + | + | + | + | + |
| NS2 | − | + | − | + | + | + | + | + |
| Virus titer (pfu/ml) | $7 \times 10^3$ | $7 \times 10^3$ | $1 \times 10^3$ | $3 \times 10^4$ | 0 | 0 | 0 | 0 |

*293T cells were transfected with the indicated plasmids. Twenty-four (Experiments 1 and 2) or forty-eight hours (Experiments 3–8) later, the virus titer in the supernatant was determined in MDCK cells.
†Unless otherwise indicated, plasmids were constructed with cDNAs representing the RNAs of A/WSN/33 virus.

Efficiency of influenza virus production with coexpression of all viral structural proteins. Although expression of the viral NP and polymerase proteins is sufficient for the plasmid-driven generation of influenza viruses, it was possible that the efficiency could be improved. In previous studies, the expression of all influenza virus structural proteins (PB2, PB1, PA, HA, NP, NA, M1, M2, and NS2) resulted in VLPs that contained an artificial vRNA encoding a reporter chloramphenicol-acetyltransferase gene (Mena et al., 1996). Thus, the availability of the entire complement of structural proteins, instead of only those required for viral RNA replication and transcription, might improve the efficiency of virus production. To this end, 293T cells were transfected with optimal amounts of viral protein expression plasmids (as judged by VLP production; unpublished data): 1 µg of pcDNA762(PB2) and pcDNA774(PB1); 0.1 g of pcDNA787(PA); 1 µg of pEWSN-HA, pCAGGS-WSN-NP0/14, and pCAGGS-WNA15; 2 µg of pCAGGS-WSN-M1-2/1; 0.3 g of pCA-NS2; and 0.03 g of pEP24c (for M2), together with 1 g of each RNA polymerase I plasmid (Experiment 2, Table 1). A second set of cells was transfected with the same set of RNA polymerase I plasmids, with the exception of the PB 1 gene, for which pPolI-PR/8/34-PB1 was substituted in an effort to generate a reassortant virus, together with plasmids expressing only PA, PB1, PB2, and NP (Experiment 3, Table 1) or those expressing all the influenza structural proteins (Experiment 4, Table 1). Yields of WSN virus did not appreciably differ at 24 hours (Experiments 1 and 2, Table 1) or at 36 hours (data not shown) post-transfection. However, more than a 10-fold increase in yields of the virus with PR/8/34-PB1 was found when all the influenza viral structural proteins were provided (Experiments 3 and 4, Table 1). Negative controls, which lacked one of the plasmids for the expression of PA, PB1, PB2, of NP proteins, did not yield any virus (Experiments 5–8, Table 1). Thus, depending on the virus generated, expression of all influenza A virus structural proteins appreciably improved the efficiency of the reverse genetics method.

Next, the kinetics of virus production after transfection of cells was determined using the set of plasmids used to generate a virus with the A/PR/8/34-PB1 gene. In two of three experiments, virus was first detected at 24 hours after transfection. The titer measured at that time, >$10^3$ pfu/ml, had increased to >$10^6$ pfu/ml by 48 hours after transfection (Table 2). To estimate the percentage of plasmid-transfected cells that were producing viruses, 293T cells were treated with EDTA (0.02%) at 24 hours after transfection to disperse the cells, and then performed limiting dilution studies. In this experiment, no free virus was found in the culture supernatant at this time point. The results indicated that 1 in $10^{33}$ cells was generating infectious virus particles.

TABLE 2

Kinetics of virus production after plasmid transfection into 293T cells*

| Hours after plasmid transfection | Virus titers in culture supernatant (pfu/ml) Experiment | | |
|---|---|---|---|
| | 1 | 2 | 3 |
| 6 | 0 | ND | ND |
| 12 | 0 | ND | 0 |
| 18 | 0 | ND | 0 |
| 24 | 0 | $2 \times 10^3$ | $6 \times 10^3$ |
| 30 | ND | $5 \times 10^4$ | $9 \times 10^4$ |
| 36 | $6 \times 10^2$ | >$1 \times 10^5$ | $7 \times 10^5$ |
| 42 | ND | >$1 \times 10^6$ | $5 \times 10^6$ |
| 48 | $8 \times 10^4$ | >$1 \times 10^6$ | $1 \times 10^7$ |

*293T cells were transfected with eight RNA polymerase I plasmids encoding A/WSN/33 virus genes with the exception of PB1 gene, which is derived from A/PR/8/34 virus, and nine protein expression plasmids as described in the text. At different time points, we titrated virus in the culture supernatant in MDCK cells.
ND = not done.

Figure 4:
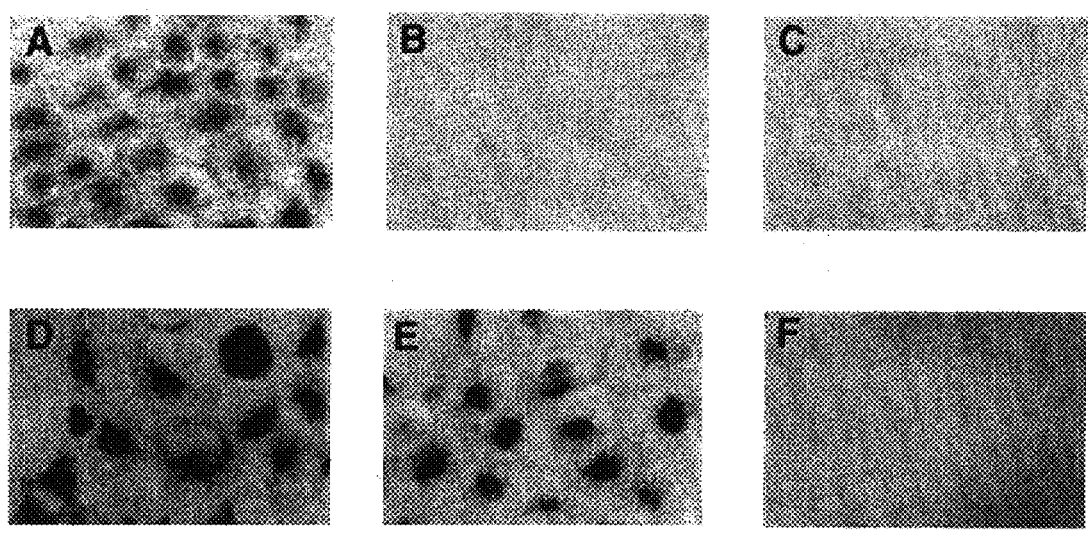
FIG. 4. Detection of the FLAG epitope in cells infected with a transfectant virus. Antibody staining was used to identify the NA in MDCK cells infected with either PR8-WSN-FL79 (A, D) or A/WSN/33 wild-type virus (B, E), or on mock-infected MDCK cells (C, F). Nine hours after infection, cells were fixed with paraformaldehyde, treated with Triton X-100 and incubated with either anti-FLAG (A–C) or anti-WSN NA (D–F) monoclonal antibodies. Intensive Golgi staining (red) is apparent in positive samples (A, D, and E).

Recovery of influenza virus containing the FLAG epitope in the NA protein. To verify that the new reverse genetics system allowed the introduction of mutations into the genome of influenza A viruses, a virus containing a FLAG epitope (Castrucci et al., 1992) in the NA protein was generated. 293T cells were transfected with an RNA polymerase I plasmid (pPolI-WSN-NA/FL79) that contained a cDNA encoding both the NA protein and a FLAG epitope at the bottom of the protein's head, together with the required RNA polymerase I and protein expression plasmids. To confirm that the recovered virus (PR8-WSN-FL79) did in fact express the NA-FLAG protein, immunostaining assays of cells infected with PR8-WSN-FL79 or A/WSN/33 wild-type virus was performed. A monoclonal antibody to the FLAG epitope detected cells infected with PR8-WSN-FL79, but not those infected with wild-type virus (FIG. 4). Recovery of the PR8-WSN-FL79 virus was as efficient as that for the untagged wild-type virus (data not shown). These results indicate that the new reverse genetics system allows one to introduce mutations into the influenza A virus genome.

Generation of infectious influenza virus containing mutation, in the PA gene. To produce viruses possessing mutations in the PA gene, two silent mutations were introduced creating new recognition sequences for restriction endonucleases (Bsp120I at position 846 and PvuII at position 1284 of the mRNA). Previously, it was not possible to modify this gene by reverse genetics, because of the lack of a reliable selection system. Transfectant viruses, PA-T846C and PA-A1284 were recovered. The recovered transfectant viruses were biologically cloned by two consecutive limiting dilutions. To verify that the recovered viruses were indeed transfectants with mutations in the PA gene, cDNA for the PA gene was obtained by reverse transcriptase-PCR. As shown in FIG. 5, PA-T846C and PA-A1284C viruses had the expected mutations within the PA gene, as demonstrated by the presence of the newly introduced restriction sites. PCR of the same viral samples and primers without the reverse transcription step failed to produce any products (data not shown), indicating that the PA cDNA was indeed originated from vRNA instead of the plasmid used to generate the viruses. These results illustrate how viruses with mutated genes can be produced and recovered without the use of helper viruses.

Discussion

The reverse genetics systems described herein allows one to efficiently produce influenza A viruses entirely from cloned cDNAs. Bridgen and Elliott (1996) also used reverse genetics to generate a Bunyamwera virus (Bunyaviridae family), but it contains only three segments of negative-sense RNA, and the efficiency of its production was low, $10^2$ pfu/$10^7$ cells. Although the virus yields differed among the experiments, consistently >$10^3$ pfu/$10^6$ cells was observed for influenza virus, which contains eight segments. There are several explanations for the high efficiency of the reverse genetics system described hereinabove. Instead of producing RNPs in vitro (Luytjes et al., 1989), RNPs were generated in vivo through intracellular synthesis of vRNAs using RNA polymerase I and through plasmid-driven expression of the viral polymerase proteins and NP. Also, the use of 293T cells, which are readily transfected with plasmids (Goto et al., 1997), ensured that a large population of cells received all of the plasmids needed for virus production. In addition, the large number of transcripts produced by RNA polymerase I, which is among the most abundantly expressed enzymes in growing cells, likely contributed to the overall efficiency of the system. These features led to a correspondingly abundant number of vRNA transcripts and adequate amounts of viral protein for encapsidation of vRNA, formation of RNPs in the nucleus, and export of these complexes to the cell membrane, where new viruses are assembled and released.

Previously established reverse genetics systems (Enami et al., 1990; Neumann et al., 1994; Luytjes et al., 1989; Pleschka et al., 1996) require helper-virus infection and therefore selection methods that permit a small number of transfectants to be retrieved from a vast number of helper viruses. Such strategies have been employed to generate influenza viruses that possess one of the following cDNA-derived genes: PB2 (Subbarao et al., 1993), HA (Enami et al., 1991: Horimoto et al., 1994), NP (Li et al., 1995), NA (Enami et al., 1990), M (Castrucci et al., 1995; Yasuda et al., 1994), and NS (Enami et al., 1991). Most of the selection methods, except for those applicable to the HA and NA genes, rely on growth temperature, host range restriction, or drug sensitivity, thus limiting the utility of reverse genetics for functional analysis of the gene products. Even with the HA and NA genes, for which reliable antibody-driven selection systems are available, it is difficult to produce viruses with prominent growth defects. In contrast, the reverse genetics system described herein does not require helper virus and permits one to generate transfectants with mutations in any gene segment or with severe growth defects. This advantage is demonstrated in FIG. 5, which the recovery of transfectant viruses with a mutated PA gene. Having the technology to introduce any viable mutation into the influenza A virus genome will enable investigators to address a number of long-standing issues, such as the nature of regulatory sequences in nontranslated regions of the viral genome, structure-function relationships of viral proteins, and the molecular basis of host-range restriction and viral pathogenicity.

Although inactivated influenza vaccines are available, their efficacy is suboptimal due partly to their limited ability to elicit local IgA and cytotoxic T cell responses. Clinical trials of cold-adapted live influenza vaccines now underway suggest that such vaccines are optimally attenuated, so that they will not cause influenza symptoms, but will still induce protective immunity (reviewed in Keitel & Piedra, 1998). However, preliminary results indicate that these live virus vaccines will not be significantly more effective than the best inactivated vaccine (reviewed in Keitel. & Piedra, 1998), leaving room for further improvement. One possibility would be to modify a cold-adapted vaccine with the reverse genetics system described above. Alternatively, one could start from scratch by using reverse genetics to produce a "master" influenza A strain with multiple attenuating mutations in the genes that encode internal proteins. The most intriguing application of the reverse genetics system described herein may lie in the rapid production of attenuated live-virus vaccines in cases of suspected pandemics involving new HA or NA subtypes of influenza virus.

This new reverse genetics system will likely enhance the use of influenza viruses as vaccine vectors. The viruses can be engineered to express foreign proteins or immunogenic epitopes in addition to the influenza viral proteins. One could, for example, generate viruses with foreign proteins as a ninth segment (Enami et al., 1991) and use them as live vaccines. Not only do influenza viruses stimulate strong cell-mediated and humoral immune responses, but they also afford a wide array of virion surface HA and NA proteins (e.g., 15 HA and 9 NA subtypes and their epidemic variants), allowing repeated immunization of the same target population.

Influenza VLPs possessing an artificial vRNA encoding a reporter gene have been produced by expressing viral structural proteins and vRNA with the vaccinia-T7 polymerase system (Mena et al., 1996). Using reverse genetics, one can now generate VLPs containing vRNAs that encode proteins required for vRNA transcription and replication (i.e., PA, PB1, PB2, and NP), as well as vRNAs encoding proteins of interest. Such VLPs could be useful gene delivery vehicles. Importantly, their lack of genes encoding viral structural proteins would ensure that infectious viruses will not be produced after VLP-gene therapy. Since the influenza virus genome is not integrated into host chromosome, the VLP system would be suitable for gene therapy in situations requiring only short-term transduction of cells (e.g., for cancer treatment). In contrast to adenovirus vectors (Kovesdi et al., 1997), influenza VLPs could contain both HA and NA variants, allowing repeated treatment of target populations.

The family Orthomyxoviridae comprises influenza A, B, and C viruses, as well as the recently classified Thogotovirus. The strategy for generating infectious influenza A viruses entirely from cloned cDNAs described herein would apply to any orthomyxovirus, and perhaps to other segmented negative-sense RNA viruses as well (e.g., Bunyaviridae, Arenaviridae). The ability to manipulate the viral genome without technical limitations has profound implications for the study of viral life cycles and their regulation, the function of viral proteins and the molecular mechanisms of viral pathogenicity.

EXAMPLE 2

Materials and Methods

Cells and viruses. 293T human embryonic kidney cells and Madin-Darby canine kidney cells (MDCK) were maintained in DMEM supplemented with 10% FCS and in MEM containing 5% newborn calf serum, respectively. The 293T cell line is a derivative of the 293 line, into which the gene for the simian virus 40 T antigen was inserted (DuBridge et al., 1987). All cells were maintained at 37° C. in 5% $CO_2$. Influenza virus A/Udorn/307/72 ($H_3N_2$) (Udorn) was propagated in 10-day-old eggs.

Construction of plasmids. The cDNA of Udorn virus was synthesized by reverse transcription of viral RNA with an oligonucleotide complementary to the conserved 3' end of viral RNA, as described by Katz et al. (1990). The cDNA was amplified by PCR with M gene-specific oligonucleotide primers containing BsmBI sites, and PCR products were cloned into the pT7Blueblunt vector (Novagen, Madison, Wis.). The resulting construct was designated pTPolIUdM. After digestion with BsmBI, the fragment was cloned into the BsmBI sites of the pHH21 vector, which contains the human RNA polymerase I promoter and the mouse RNA polymerase I terminator, separated by BsmBI sites (Neumann et al., 1999), resulting in pPolIUdM. Plasmids derived from pHH21 for the expression of vRNA are referred to as "PolI" constructs in this report.

The M mutants were constructed as follows. pTPolIUdM was first amplified by inverse PCR (Ochman et al., 1988) using the back-to-back primers M2104R (5'-AAGAGG GTCACTTGAATCG-3'; SEQ ID NO:1) and M2V27T (5'-ACTGTTGCTGCGAGTATC-3'; SEQ ID NO:2) and M2A30P (5'-GTTGTTGCTCCAACTATC-3'; SEQ ID NO:3) and M2S3 IN (5'-GTTGTTGCTGCGAACATC-3'; SEQ ID NO:4) and M2del29-31 (5'-GTTGTTATCATTGGATCTTGC-3'; SEQ ID NO:5), and the back-to-back primers M2128R (5'-CCCAATGATACTCGCAGC-3'; SEQ ID NO:6) and M2W41A (5'-ATCTTGCACTTGATATTGGCAATTC-3'; SEQ ID NO:7), and the back-to-back primers M2HATMR (5'-CACCAGTGAACTGGCGACAGTTGAGTA-GATCGCCAGAATGTCACTTGAA TCGTTGCATCTGC-3'; SEQ ID NO:8) and M2HATM (5'-

CTTTTGGTCTCCCTGGGGGCAATCAGTTTCTGGAT GGATCGTCTTTTTC AAATGC-3'; SEQ ID NO:9), and M2NATMR (5'-GCTTAGTATCAATTGTATTCCATTTAT-GAJTGATATCCAAATGCTGTCAC TTGAATCGTTGCATCTGC-3'SEQ ID NO:10) and M2NATM (5'-ATTATAGGAGTCGTAATGTGTATCT-CAGGGATTACCATAATAGATCGTCT TTTTITCAAATGC-3'; SEQ ID NO:11).

The PCR products were phosphorylated, self-ligated, and propagated in E. coli strain DH5α, and then digested with BsmBI and cloned into the BsmBI sites of the pHH21 vector. The resulting constructs were designated pPolIM2V27T, pPolIM2A30P, pPolIM2S31N, pPolIM2del29-31, pPolIM2W41A, pPolM2HATM, and pPolIM2NATM. All of the constructs were sequenced to ensure that unwanted mutations were not present. The plasmids for the expression of the HA (pEWSN-HA), NP (pCAGGS-WSN-NP0/14), NA (pCAGGS-WNA15), M1 (pCAGGS-WSN-M1-2/1) proteins of A/WSN/33 (H1N1) virus, and the M2 (pEP24c), NS2 (pCANS2), PB1 (pcDNA774), PB2 (pcDNA762), and PA (pcDNA787) of A/Puerto Rico/8/34 (H1N1) virus are described in Neumann et al. (1999).

Plasmid-driven Reverse Genetics. Transfectant viruses were generated as reported in Neumann et al. (1999). Briefly, 17 plasmids (8 PolI constructs for 8 RNA segments and 9 protein-expression constructs for 9 structural proteins) were mixed with transfection reagent (2 1 of Trans IT LT-1 (Panvera, Madison, Wis.) per g of DNA), incubated at room temperature for 15 minutes, and added to $1 \times 10^6$ 293T cells. Six hours later, the DNA-transfection reagent mixture was replaced by Opti-MEM (GIBCO/BRL) containing 0.3% BSA and 0.01% FCS. Forty-eight hours later, viruses in the supernatant were plaque-purified in MDCK cells once and then inoculated into MDCK cells for the production of stock virus. The M genes of transfectant viruses were sequenced to confirm the origin of the gene and the presence of the intended mutations and to ensure that no unwanted mutations were present. In all experiments, the transfection viruses contained only the M gene from Udorn virus and the remaining genes from A/WSN/33.

Replicative properties of the transfectant viruses. MDCK cells in duplicate wells of 24-wells plates were infected with wild-type and mutant viruses at a multiplicity of infection (MOI) of 0.001 plaque-forming units (PFU) per cell, overlaid with MEM medium containing 0.5 μg of trypsin per ml, and incubated at 37° C. At different times, supernatants were assayed for infectious virus in plaque assays on MDCK cells.

To investigate the amantadine sensitivity of mutant viruses, the viruses were titrated in MDCK cells in the presence of different concentrations of the drug.

M2 incorporation into viruses. Transfectant viruses were grown in MDCK cells containing 0.5 μg of trypsin per ml. Viruses were purified through six-step sucrose gradients (20, 30, 35, 40, 45, and 50%) for 2.5 hours at 50,000 g at 4° C. Virus was resuspended in PBS and stored in aliquots at −80° C. Purified virus was resuspended in the lysis buffer (0.6 M KCl, 50 mM Tris-Cl [pH 7.5], 0.5% Triton X-100). The viral lysates were placed on 15% SDS-polyacrylamide gels, which then were electrotransferred to polyvinylidene difluoride (PVDF) membrane. The membrane was blocked overnight at 4° C. with 5% skimmed milk in PBS, and then incubated with the 14C2 anti-M2 monoclonal antibody (kindly provided by Dr. R. Lamb) and anti-WSN-NP monoclonal antibody for 1 hour at room temperature. The membrane was washed three times with PBS containing 0.05% Tween-20. Bound antibodies were detected with a VECTASTAIN ABC kit (Vector) and the Western immuno-blot ECL system (Amersham). Signal intensities were quantified with an Alpha Imager 2000 (Alpha Innotech Corporation).

Experimental infection. Five-week-old female BALB/c mice, anesthetized with isoflurane, were infected intranasally with 50 μl ($5.0 \times 10^3$ PFU) of virus. Virus titers in organs were determined 3 days after infection with MDCK cells, as described (Bilsel et al., 1993).

Results

Figure 7:
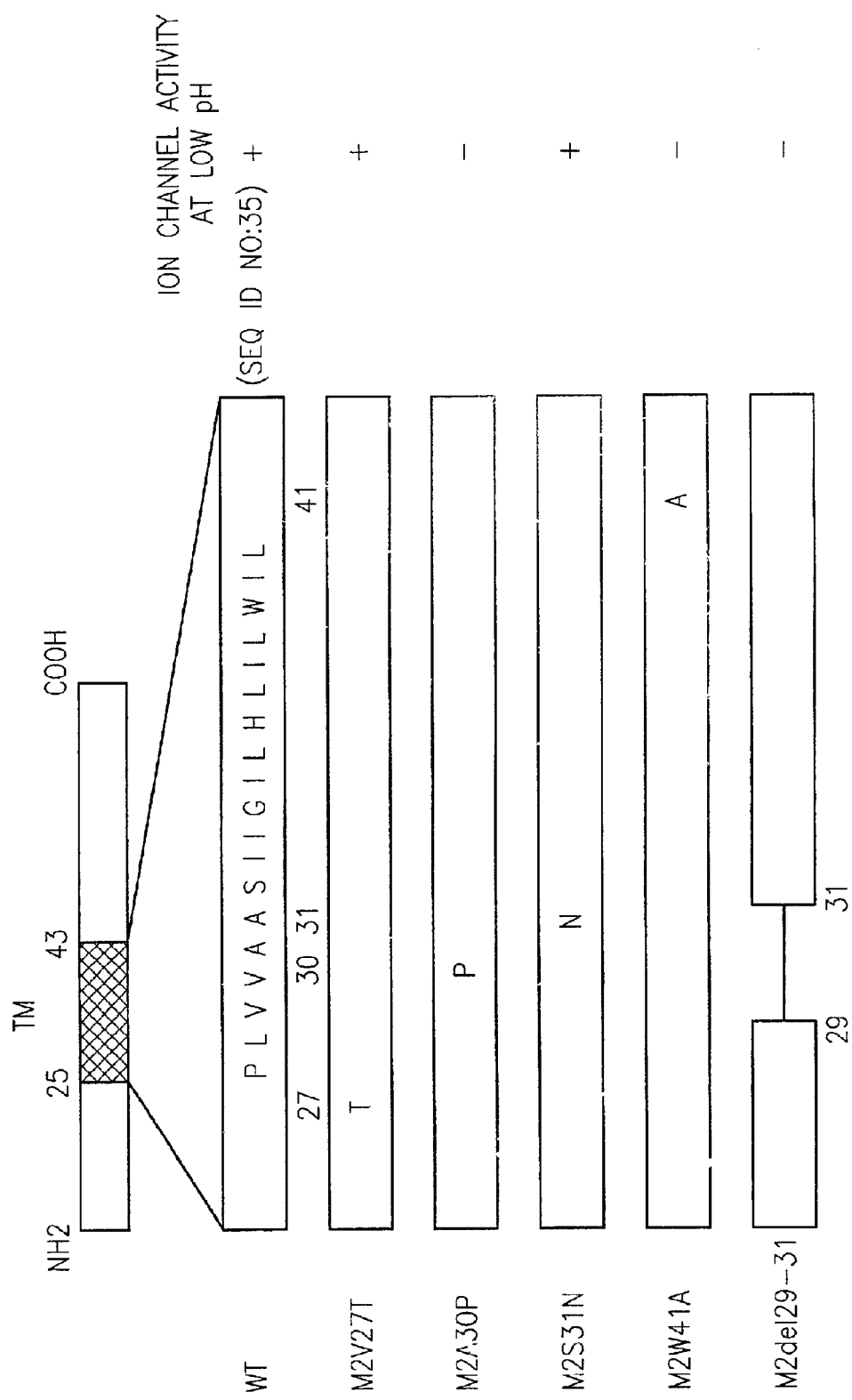
FIG. 7. Schematic diagram of mutant influenza virus M2 proteins and their properties. The amino acid sequence of the TM domain (residues 25 to 43) is shown in single-letter code in the expanded section of the diagram. The ion channel activity was determined by Holdinger et al. (1994), using a two-electrode voltage-clamp procedure. +, detectable ion channel activity; –, nondetectable ion channel activity.

Generation of influenza A viruses containing mutations in the M2 protein. The TM domain of the M2 protein is modeled to have an α helical structure (Duff et al., 1992; Sugrue and Hay, 1991; Sansom and Kerr, 1993). Mutations at residues V-27, A-30, S-31, G-34, and L-38, all of which are located on the same face of the α helix, alter the properties of the M2 ion channel (Grambas et al., 1992; Pinto et al., 1992; Wang et al., 1993). To determine whether the ion channel activity of M2 is essential for viral replication, five plasmids were constructed and used to generate mutant viruses possessing changes in the M2 TM domain (FIG. 7). The whole-cell currents of the mutant proteins expressed in oocytes of Xenopus laevis, were measured by Holsinger et al. (1994), using a two-electrode voltage-clamp procedure. None of three mutants, i.e., M2A30P, M2W41A, and M2del29-31, had functional ion channel activity at either neutral or low pH. M2V27T and M2S31N, which showed ion channel activity at low pH (Holsinger et al., 1994), were used as positive controls.

To generate mutant viruses by plasmid-driven reverse genetics (Neumann et al., 1999), 293T cells were transfected with nine protein-expression plasmids and eight others for the production of viral RNA segments that encoded all A/WSN/33 (H1N1) viral genes except the M gene, which was derived from the A/Udorn/307/72 (H3N2) (Udorn) virus (wild-type). The corresponding transfectant viruses were designated M2V27T, M2A30P, M2S3 IN, M2W41 A, M2del29-31, and WSN-UdM, for the virus containing the parental Udorn M gene.

To determine the efficiency of virus generation, viruses were titrated in the culture supernatant of 293T cells at 48 hours post-transfection using MDCK cells. As shown in Table 3, more than 105 transfectant viruses with the wild-type or mutant M gene were present. Thus, all viruses bearing M2 mutations and the virus possessing the wild-type Udorn M gene were generated with similar efficiency. The transfectant viruses were plaque-purified once in MDCK cells and then inoculated into MDCK cells to make virus stocks. The stability of the introduced mutations was analyzed by sequencing the M gene segments of the transfectant viruses after ten passages in MDCK cells. No revertants were found.

TABLE 3

Virus titers in the supernatant of 293T cells after plasmid transfection[a]

| Virus | Titers (PFU/ml) |
|---|---|
| Wild type | $1.9 \times 10^5$ |
| M2V27T | $6.0 \times 10^5$ |
| M2A30P | $1.1 \times 10^5$ |
| M2S31N | $1.2 \times 10^6$ |
| M2W41A | $1.2 \times 10^6$ |
| M2del29-31 | $1.7 \times 10^6$ |

TABLE 3-continued

Virus titers in the supernatant of 293T cells after plasmid transfection[a]

| Virus | Titers (PFU/ml) |
|---|---|
| M2HATM | $2.2 \times 10^4$ |
| M2NATM | $2.2 \times 10^3$ |

[a]293T cells were transfected with eight plasmids for the production of A/WSN/33 vRNA (excluding the M gene, which was derived form A/Udorn/72 virus) and nine protein expression plasmids, as described in Materials and Methods. At 48 hours posttransfection, virus in the supernatant of 293T cell cultures was titrated using MDCK cells.

Figure 8:
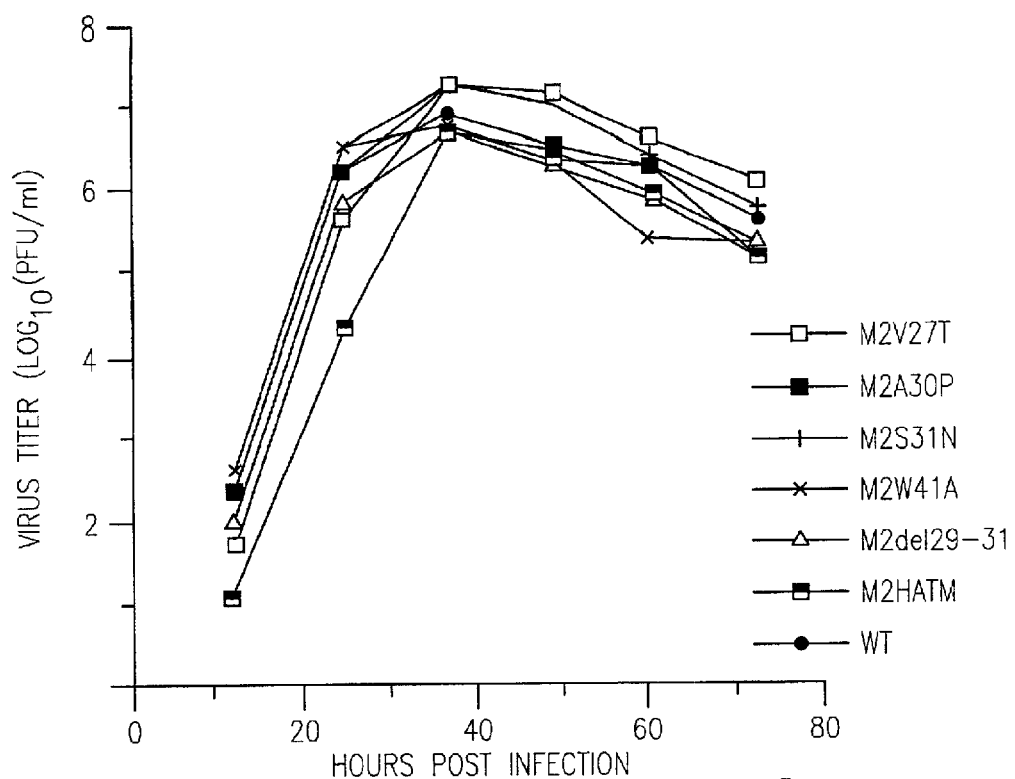
FIG. 8. Growth curves of the M2 mutant and wild-type WSN-UdM viruses. MDCK cells were infected with virus at an MOI of 0.001. At the indicated times after infection, the virus titer in the supernatant was determined. The values are means of triplicate experiments. The SD is less than 0.59 for each sample.

Growth properties of M2 mutant viruses in tissue culture. Next, the growth properties of M2 ion channel mutants and wild-type WSN-UdM virus in MDCK cells were compared (FIG. 8). Cells were infected at an MOI of 0.001, and yields of virus in the culture supernatant were determined at different times postinfection. The mutant viruses did not differ appreciably from the wild-type WSN-UdM virus in either growth rate or the size of plaques formed at 48 hours (1.5 mm in diameter in 3 days).

Figure 9:
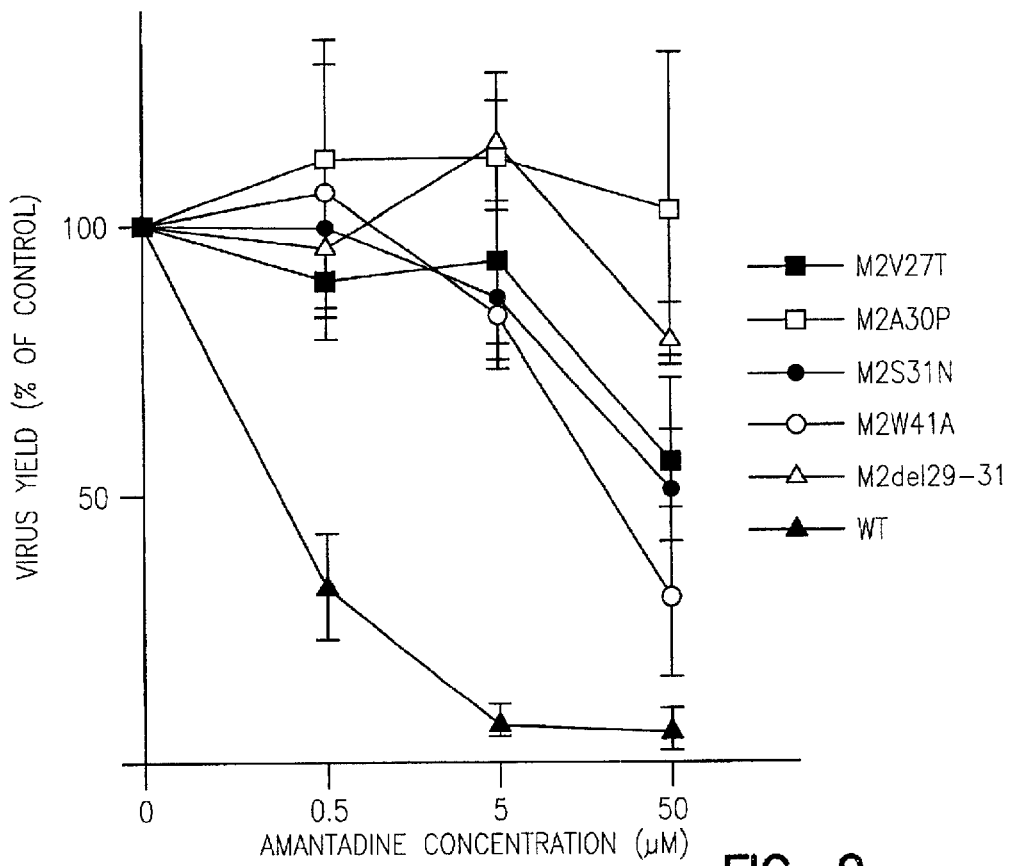
FIG. 9. Amantadine sensitivity of the M2 ion channel mutants. The mutant and wild-type WSN-UdM viruses were tested for plaque-forming capacity in MDCK cells in the presence of different concentrations of amantadine. Experiments were performed three times, with the results reported as means SD.

To assess the amantadine sensitivity of these viruses, the M2 mutants and wild-type WSN-UdM viruses were plaqued in MDCK cells in the presence of different concentrations of amantadine. In cell culture, amantadine produces two discrete concentration-dependent inhibitory actions against viral replication. A nonspecific action at concentrations >50 M, resulting from an increase in the pH of endosomes, inhibits activation of HA membrane fusion activity involved in endocytosis (Daniels et al., 1985); whereas at lower concentrations, 0.1–5 M, the drug selectivity inhibits viral replication (Appleyard, 1977). As shown in FIG. 9, amantadine markedly reduced the yield of wild-type WSN-UdM virus, as well as the size of plaques, at each of the three test concentrations. By contrast, at 5 $\mu$M of amantadine, the replication of M2 mutant viruses was either not affected or inhibited only slightly. Substantial inhibition; due to the drug's nonspecific activity, was seen at 50 $\mu$M. Thus, all of the M2 mutants were more resistant to amantadine than the wild-type virus.

Generation of transfectant viruses in which the M2 TM domain was =laced with that from the HA or NA. Although the M2A30P, M2W41 A, and M2del29-31 mutants do not have functional ion channel activity, as assayed by a two-electrode voltage-clamp procedure (Holsinger et al., 1994), they all replicated as well as the wild-type virus in MDCK cells (FIG. 8). Thus, M2 ion channel activity may not be essential for virus replication, although it could not be ruled out that low-level ion channel activity was below the sensitivity of the assay.

Figure 10:
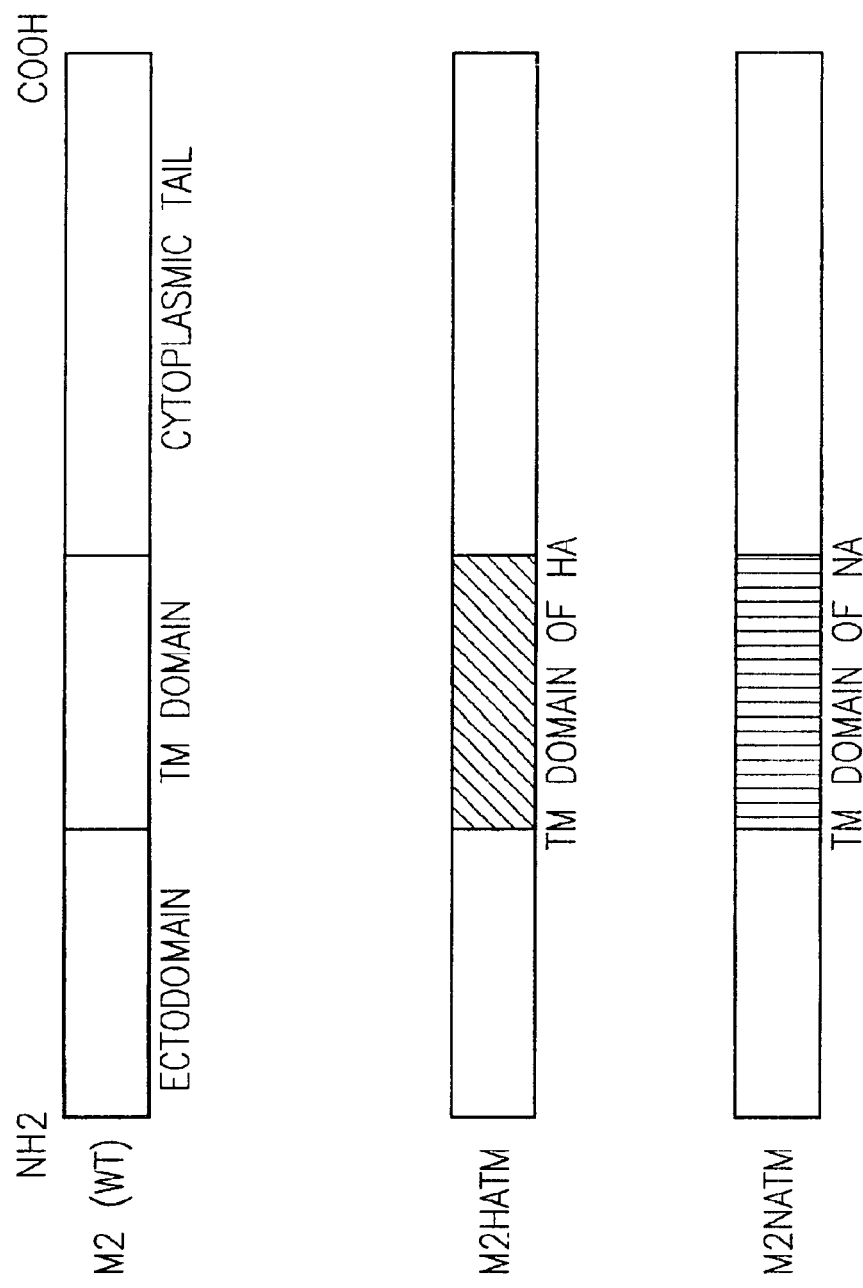
FIG. 10. Schematic diagram of the chimeric M2 mutants. Each mutant was constructed by replacing the TM domain of M2 with that of the HA or NA.

To determine whether M2 channel ion activity is not essential for viral replication, chimeric mutant viruses were generated in which the M2 TM domain was replaced with that from the HA or NA of the A/WSN/33 virus (FIG. 10). When the supernatant of 293T cells which had been transfected with plasmids was assayed for virus production, the chimeric mutants (M2HATM and M2NATM) were each viable, but their titers were more than one log lower than the wild-type WSN-UdM titer (Table 3). The mutants also produced pinpoint plaques after 48 hours of growth. Thus, the M2 TM domain is dispensable for viral replication in vitro.

Growth properties of the M2HATM mutant in tissue culture. Because the titers of the M2NATM virus stock did not exceed 104 PFU/ml, the M2HATM virus was employed for further analysis, first by examining the time course of progeny virus production by M2HATM versus wild-type WSN-UdM viruses in MDCK cells (FIG. 8). Although M2HATM produced a lower titer than did the wild-type WSN-UdM virus at 12 and 24 hours postinfection, its maximum titer at 36 hours was almost the same as that of the wild-type virus. This result indicates that the absence of the M2 TM domain does not drastically impair the replicative ability of the virus in tissue culture.

Figure 11:
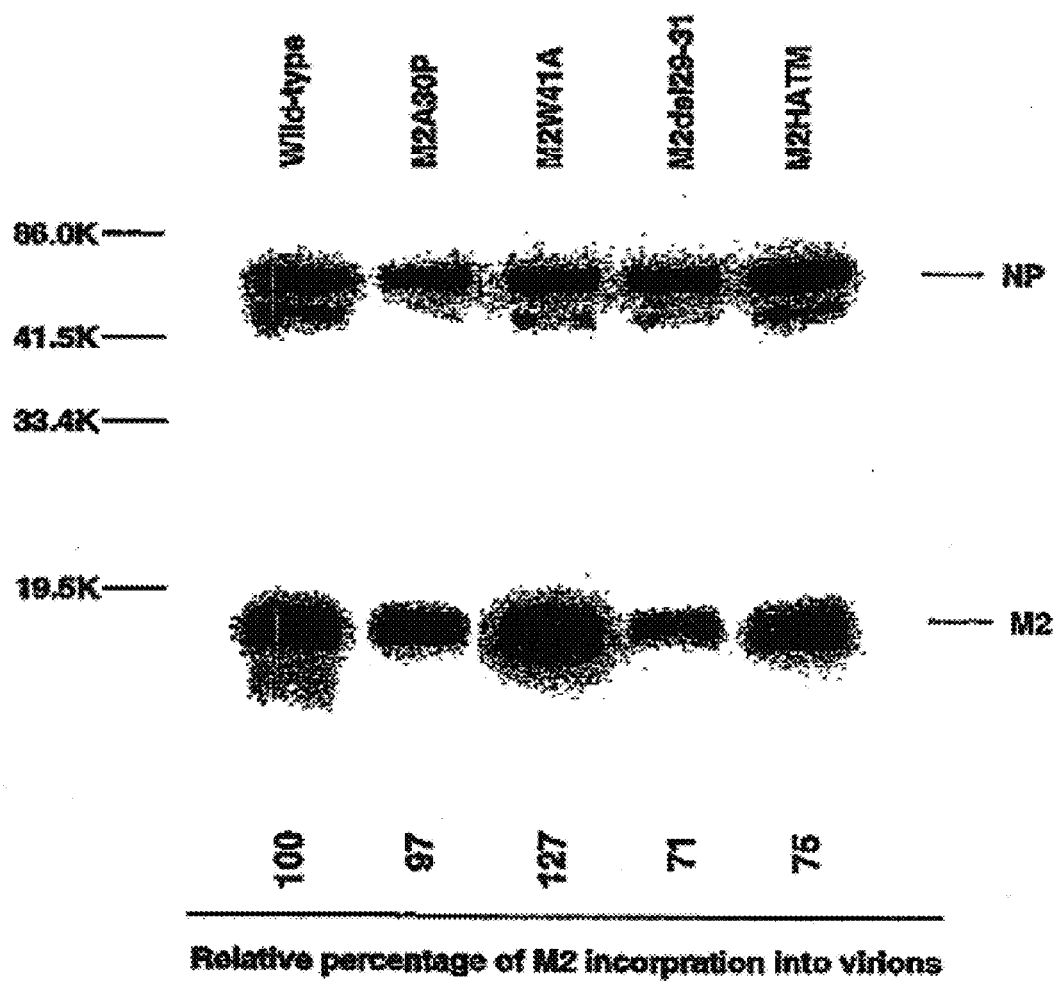
FIG. 11. Incorporation of the M2 mutants into influenza virions. Purified viruses were lysed in a sample buffer. Viral proteins were treated with 2-mercaptoethanol, separated by 15% SDS-PAGE, transferred to a PVDF membrane, and detected with the 14C2 anti-M2 monoclonal antibody (Zebedee and Lamb, 1988) and anti-WSN-NP monoclonal antibody. Molecular masses of the marker proteins are shown on the left.

Incorporation of mutant M2 molecules into virions. Conceivably, the M2 point and chimeric mutants possessed some residual ion channel activity, so that increased incorporation of the M2 protein into virions could compensate for any defect in this function. Therefore, the efficiency of incorporation of the wild-type and mutant M2s into influenza virions was compared using Western blot analysis after standardization based on the intensity of NP (FIG. 11). Virion incorporations of two mutant M2 proteins (M2del29-31 and M2HATM) was slightly less than that of the wild-type protein, although the W41A mutant was incorporated more efficiency. The band detected slightly below the M2 protein in the wild-type is probably a proteolytically cleaved form of M2, as reported by others (Zebedee and Lamb, 1988). An additional band below the NP protein that was reactive with anti-NP, but not anti-M2 antibody, is a cleavage product of NP (Zhirnov and Bukrinskaya, 1984). Together, these results demonstrate that increased incorporation of M2 protein into virions does not seem to compensate for defective M2 ion channel activity.

Replication of M2 mutant viruses in mice. To determine the role of M2 ion channel activity in vivo, mice were infected with each of the six mutant viruses (Table 4), which replicated in the lungs as well as or more efficiently than the wild-type WSN-UdM virus, although the titer of the M2del29-31 virus was a log lower than that of the wild-type virus. By contrast, the mutants showed different replicative potentials in nasal, turbinates, with neither the M2A30P nor M2del29-31 virus recovered from such samples in any of the infected mice. M2HATM virus was not recovered from either the lungs or the nasal turbinates. These results indicate that M2 ion channel activity is necessary for efficient viral replication in vivo. Further, the serum of the infected mice have antibodies which bind to the immunizing virus (see Example 3).

TABLE 4

Replication of M2 mutants in mice[a]

| | Mean titers ($\log_{10}$PFU/g) ± SD | |
|---|---|---|
| Virus | Nasal turbinate | Lung |
| Wild-type | 3.9 ± 0.5 | 6.8 ± 0.3 |
| M2V27T | 4.3 ± 0.7 | 7.3 ± 0.3 |
| M2A30P | NR[b] | 6.8 ± 0.1 |
| M2S31N | 4.3 ± 0.4 | 7.0 ± 0.2 |
| M2W41A | 3.1 ± 2.2[c] | 6.7 ± 0.2 |
| M2del29-31 | NR | 5.6 ± 0.1 |
| M2HATM | NR | NR |

[a]Five-week-old female BALB/c mice (n = 4), anesthetized with isofluorane, were infected intranasally with 50 $\mu$l of virus (5 × 10³ PFU). Virus titers in organs were determined 3 days after infection with MDCK cells.
[b]NR, virus was not recovered from any of the infected mice (less than $10^2$ PFU/g).
[c]Virus was recovered from only three of the four mice infected.

Discussion

A reverse-genetics system (Neumann et al., 1999) was used to generate transfectant influenza A viruses with changes in the M2 protein TM domain that are known to block ion channel activity. Despite this functional defect, all of the mutant viruses replicated as efficiently as the wild-type WSN-UdM virus in vitro. The dispensability of M2 ion channel activity in viral replication was reinforced by experiments in which the TM domain of the M2 protein was replaced with that from the HA or NA. Thus, in in vitro studies, influenza A viruses did not require M2 ion channel activity for efficient replication.

M2 ion channel activity is believed to function at an early stage in the viral life cycle, between the steps of host cell penetration and uncoating of viral RNA. Zhirnov et al. (1990) reported that low pH induces the dissociation of M1 protein from viral RNPs in vitro. This observation lead others to suggest that the introduction of protons into the interior of virions through M2 ion channel activity in the endosomes is responsible for M1 dissociation from RNP (reviewed by Helenius, 1992). If so, how could this process occur in the absence of M2 ion channel activity or the M2 TM domain? Immunoelectron microscopy of the HA protein in virosomes exposed to low pH demonstrated that, in the absence of target membranes, the N-terminal fusion peptide of the HA2 subunit was inserted into the same membrane site where HA was anchored (Wharton et al., 1995). Therefore, one possibility is that the fusion peptide of the HA maybe inserted into the viral envelope, forming pores in the viral membrane that permit the flow of protons from the endosome into virus interior, resulting in disruption of RNP-M1 interaction. Alternatively, M1 may be able to dissociate from RNP by an entirely different mechanism, including ion channel activity by the TM regions of other viral membrane proteins, such as the HA, the NA or both.

What is the origin of the M2 ion channel? The M2 ion channel activity was originally discovered with A/fowl plague/Rostock/34 (FPV Rostock) strain, which has intracellularly cleavable HA (Sugreu et al., 1990; Ohuchi et al., 1994; Takeuchi and Lamb, 1994). In this strain, the HA undergoes a low pH-induced conformational change in the trans-Golgi network in the absence of M2 ion channel activity, which raises the pH in this compartment. Hence, in the past, influenza A viruses may have been equipped with an M2 protein that promoted an increase in the pH of the trans-Golgi network, to a level above which conformational changes occur in the intracellularly cleavable HA. As influenza A viruses without intracellularly cleavable HAs began to appear, there was less selective pressure to maintain high ion channel activity associated with the M2 protein. Consequent decreases in this activity may have been sufficient to allow dissociation of M1 from RNP. Indeed, ion channel activity differs markedly among the M2 proteins of currently recognized viruses: for example, fivefold more M2 protein from human Udorn virus (containing intracellularly uncleavable HA) is needed to produce the same ion channel activity displayed by an equivalent amount of M2 from FPV Rostock virus (containing intracellularly cleavable HA) (Takeuchi and Lamb, 1994). Conversely, the HAs of some influenza A viruses have changed from intracellularly uncleavable to cleavable during replication in chickens (Kawaoka et al., 1984; Horimoto and Kawaoka, 1995; Horimoto et al., 1995), suggesting that M2 protein with limited ion channel activity could acquire greater activity once a switch to intracellularly cleavable HA has occurred.

The M2 ion channel knock-out and M2HATM viruses replicated reasonably well in tissue culture, but were highly attenuated in mice, raising the possibility for their use as live vaccines. Cold-adapted live vaccines, now in clinical trials (reviewed by Maasab and Bryant, 1999), hold considerable promise for use in the general population (Sears et al., 1988; Steinhoff et al., 1991; Steinhoff et al., 1990). The major concern is that the limited number of attenuating mutations in such vaccines (Cox et al., 1988; Herlocher et al., 1993) could permit the generation of revertant viruses. Abolishing the M2 ion channel activity, for example, by replacing the M2 TM domain with that from the HA, would greatly reduce the likelihood of the emergence of revertant viruses. Thus, using our new reverse-genetics system, the generation of influenza viruses with modified viral genes could lead to the production of safe live influenza vaccines.

To date, four viral proteins have been reported to act as ion channels: M2 of influenza A virus, NB or influenza B virus, and Vpu and Vpr of human immunodeficiency virus type 1 (HIV-1) (Ewart et al., 1996; Piller et al., 1996; Pinto et al., 1992; Schubert et al., 1996; Sunstrom et al., 1996). Since the replication strategies of influenza type A and B viruses are very similar, the NB ion channel activity is also thought to play a role at an early stage of the viral life cycle, although NB still lacks a demonstrated function in viral replication. Although the Vpu protein of HIV-1 enhances the release of virus particles from cells (Schubert et al., 1995; Strebel et al., 1988; Terwilliger et al., 1989), its gene can be deleted without completely abrogating HIV-1 replication in vitro (Cohen et al., 1988; Klimkait et al., 1990; Strebel et al., 1988, 1989). Vpr, another HIV-1 auxiliary protein, is likewise not essential for replication in tissue culture (Dedera et al., 1989). Finally, here, we have shown that M2 ion channel activity is not essential for the life cycle of influenza A viruses. Therefore, ion channel activities of viral proteins may be an auxiliary function in general, although they can promote more efficient viral replication under certain conditions such as in vivo, as shown hereinabove.

EXAMPLE 3

Materials and Methods

Cells and viruses. 293T human embryonic kidney cells and Madin-Darby canine kidney (MDCK) cells were maintained in DMEM supplemented with 10% FCS and in MEM containing 5% newborn calf serum, respectively. The 293T cell line is a derivative of the 293 line, into which the gene for the simian virus 40 T antigen was inserted (Dubridge et al., 1987). All cells were maintained at 37° C. in 5% $CO_2$. M2del29-31 and WSN-UdM (wild-type) viruses were propagated in MDCK cells. A/WSN/33 (H1N1) virus was propagated in 10-day-old embryonated chicken eggs.

Immunization and protection tests. BALB/c mice (4-week-old female) were intranasally immunized with 50 μl of $1.1 \times 10^5$ PFU per ml of M2del29-31 or wild-type WSN-UdM viruses. On the second week, four mice were sacrificed to obtain sera, trachea-lung washes, and nasal washes. Two weeks and one or three months after the vaccination, immunized mice were challenged intranasally, under anesthesia, with 100 $LD_{50}$ doses of the wild-type WSN virus. For determination of virus titers, lungs were harvested at day 3 and were homogenized and titrated on MDCK cells. The remaining animals were observed for clinical signs and symptoms of infection for 14 days after challenge.

Detection of virus-specific antibody. Serum samples were examined for antibody by ELISA. In this assay, the wells were coated with purified WSN virus after treatment with 0.05 M Tris-HCl (pH 7.8) containing 0.5% Triton X-100 and 0.6 M KCl at room temperature and diluted in PBS. After incubation of virus-coated plates with test serum samples, bound antibody was detected with rabbit anti-mouse IgA (Kirkegaard & Perry Laboratories Inc., Gaithersburg, Md.) and goat anti-mouse IgG (Boehringer Mannheim, Germany) conjugated to horseradish peroxidase.

Results

In the second week after immunization, virus-specific IgG and IgA was found in nasal washes, lung washes and sera of immunized mouse. Noteably, virus specific IgG was found in greater levels in mice immunized with M2del29-31 virus in all three sample types, and virus-specific IgA was found in lung washes from M2del29-31-immunized mice but was undetectable in lung washes from WSN-UdM-immunized mice (FIG. 12).

Figures 13A, 13B, 13C:
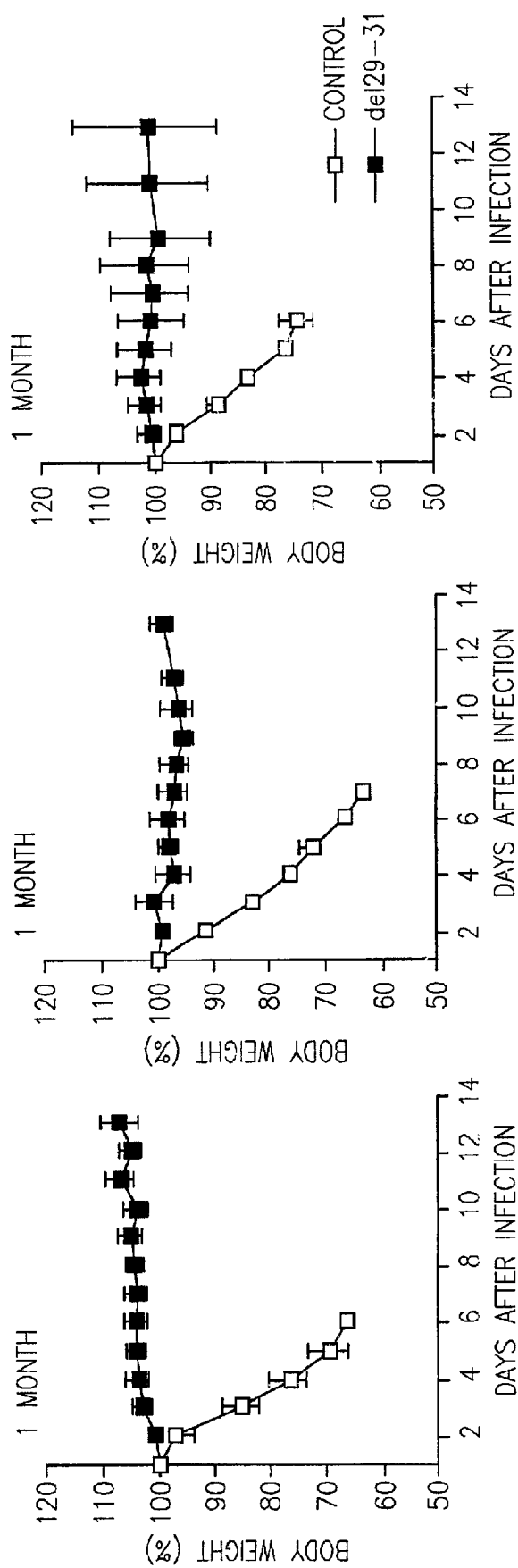
FIG. 13. Body weights of immunized mice which were challenged with wild-type virus two weeks (A), one month (B) or two months (C) after immunization.

The mice were challenged with wild-type virus two weeks, one month or two months after immunization and body weights determined for up to 2 weeks (FIG. 13). The body weights of mice immunized with M2del29-31 virus and challenged with wild-type virus remained relatively constant regardless of the timing between immunization and challenge while the body weights of mice immunized with wild-type virus and later challenged with wild-type virus dropped precipitously after challenge regardless of the timing between immunization and challenge.

The lungs from some of the mice were harvested at day 3 after challenge to determine virus titers (Table 4). Only mice that were immunized with wild-type virus and challenged with wild-type virus had detectable virus in the lungs. The lack of the presence of virus in lung of immunized mice which were challenged correlated with survival after challenge.

TABLE 4

Protection against virus challenge in immunized mice[a]

| Immunogen | No. survivors/no. tested | Virus titer in lungs [$\log_{10}$(PFU/g)] |
| --- | --- | --- |
| 2 weeks | | |
| control | 0/4 | 7.5 ± 0.1 |
| del29-31 | 4/4 | 0 |
| 1 month | | |
| control | 0/4 | 7.4 ± 0.1 |
| del29-31 | 4/4 | 0 |
| 3 months | | |
| control | 0/4 | 7.2 ± 0.1 |
| del29-31 | 4/4 | 0 |

[a]BALB/c mice (4-week-old female) were intranasally immunized with 50 µl of 1.1 × 10⁵ PFU per ml of M2del29-31 or wild-type WSN-UdM virus. Two weeks, or one or three months after the vaccination, immunized mice were challenged intranasally with 100 LD$_{50}$ doses of the wild-type WSN virus. For determination of virus titers, lungs were harvested at day 3 and were homogenized and titrated on MDCK cells. The remaining animals were observed for clinical signs and symptoms of infection for 14 days after challenge.

REFERENCES

Alberts, B., Bray, D., Lewis, J., Raff, M., Roberts, K., and Watson, J. D. (eds) *Molecular Biology of the Cell*. Garland Publishing, Inc., New York, N.Y. (1994).

Albo, C., Martin, J., and Portela, A., *J. Virol*, 70, 9013–9017 (1996).

Appleyard, G., *J. Gen. Virol.*, 36, 249–255 (1977).

Bilsel, P., Castrucci, M. R., and Kawaoka, Y., *J. Virol*, 6, 6762–6767 (1993).

Bridgen, A. and Elliot, R. M., *Proc Natl. Acad. Sci U.S.A.*, 93, 15400–15404 (1996).

Castrucci, M. R., Bilsel, P. and Kawaoka, Y., *J. Virol.*, 66, 4647–4653 (1992).

Castrucci, M. R. and Kawaoka, Y., *J. Virol.*, 69, 2725–2728 (1995).

Cox, N. J., Kitame, F., Kendal, A. P., Maassab, H. F., and Naeve, C., *Virology*, 167, 554–567 (1988).

Daniels, R. S., Downie, J. C., Hay, A. J., Knossow, M., Skehel, J. J., Wang, M. L., and Wiley, D. C., *Cell*, 40, 431–439 (1985).

Dedera, D., Hu, W., Vander Heyden, H., and Ratner, L., *J. Virol.*, 63, 3205–3208 (1989).

DuBridge, R. B., Tang, P., Hsia, H. C., Leong, P. M., Miller, J. H., and Calos, M. P., *Mol. Cell Biol.*, 7, 379–387 (1987).

Duff, K. C., and Ashley, R. H., *Virology*, 190, 485–489 (1992).

Duff, K. C., Kelly, S. M., Price, N. C., and Bradshaw, J. P., *FEBS Lett.*, 311, 256–258 (1992).

Dunn, E. F., Pritlove, D. C., Jin, H., and Elliott, R. M., *Virology*, 211, 133–143 (1995).

Enami, M., Luytjes, W., Krystal, M. and Palese, P., *Proc. Natl. Acad. Sci. U.S.A.*, 87, 3802–3805 (1990).

Enami, M., Sharma, G., Benham, C. and Palese, P., *Virology*, 185, 291–298 (1991).

Enami, M. and Palese, P., *J. Virol.*, 61, 2711–2713 (1991).

Ewald, G. D., Sutherland, T., Gage, P. W., and Cok, G. B., *J. Virol.*, 70, 7108–7115 (1996).

Grambas, S., Bennett, M. S., and Hay, A. J., Virology, 10, 541–549 (1992).

Goto, H., Bethell, R. C. and Kawaoka, Y., Virology, 238265–272 (1997).

Hagen, M., chung, T. D. Y., Butcher, J. A., and Krystal, M., *J. Virol.*, 68, 1509–1515 (1994).

Hay, A. J., Thompson, C. A., Geraghty, F. M., Hayhurst, A., Grambas, S., and Bennett, M. S., In Hannoun, C., Kendal, A. P., Klenk, H. D., and Ruben, F. L. (eds) *Options for the control of influenza II*. Excerpta Medica, Amsterdam, pp. 281–288 (1993).

Hay, A. J., Wolstenholme, A. J., Skehel, J. J., and Smith, M. H., *EMBO. J.*, 4, 3021–3024 (1985).

Helenius, A., *Cell*, 69, 577–578. (1992).

Herlocher, M. L., Maassab, H. F., and Webster, R. G., *Proc. Natl. Acad. Sci. USA*, 90, 6032–6036 (1993).

Holsinger, L. J., Nichani, D., Pinto, L. H., and Lamb, R. A., *J. Virol*, 68, 1551–1563 (1994).

Horimoto, T. and Kawaoka, Y., *J. Virol.*, 68, 3120–3128 (1994).

Horimoto, T. and Kawaoka, Y., Virology, 206, 755–759 (1995).

Horimoto, T., Rivera, E., Pearson, J., Sanne, D., Krauss, S., Kawaoka, Y., and Webster, R. G., *Virology*, 213, 223–230 (1995).

Kato, N., and Eggers, H. *J.*, *Virology*, 37, 632–641 (1969).

Katz, J. M., Wang, M., and Webster, R. G., *J. Virol.*, 64, 1808–1811 (1990).

Kawaoka, Y., Naeve, C. W., and Webster, R. G., *Virology*, 139, 303–316 (1984).

Keitel, W. A. and Piedra, P. A., in *Textbook of Influenza*, eds. Nickolson, K. G., Webster, R. G., and Hay, A. (Blackwell, Oxford), pp. 373–390 (1998).

Klimkait, T., Strebel, K., Hoggan, M. D., Martin, M. A., and Orenstein, J. M., *J. Virol*, 64, 621–629 (1990).

Lamb, R. A., and Krug, R. A., In Fields, B. N., Knipe, D. M., and Howley, P. M. (eds) *Fields Virology*, 3rd ed. Lippincott-Raven Publishers, Philadelphia, Pa., pp. 1353–1395 (1996).

Leahy, M. B., Dessens, J. T., and Nuttall, P. A., *J. Virol.*, 71, 8347–8351 (1997).

Leahy, M. B., Dessens, J. T., and Nuttall, P. A., *J. Virol.*, 71, 8352–8356 (1997).

Leahy, M. B., Dessens, J. T., Pritlove, D. C., and Nuttall, P. A., *J. Virol.*, 72, 2305–2309 (1998).

Li, S., Xu, M. and Coelingh, K., *Virus Res.*, 37, 153–161 (1995).

Luytjes, W., Krystal, M., Enami, M., Parvin, J. D. and Palese, P., *Cell*, 59, 1107–1113 (1989).

Martin, K., and Helenius, A., Cell, 67, 117–130 (1991).

Maassab, H. F., and Bryant, M. L., Rev. Med. Virol, 9, 237–244 (1991).
Mena, I., Vivo, A., Perez, E. and Portela, A., J. Virol., 70, 5016–5024 (1996).
Neirynck, S., Deroo, T., Saelens, X., Vanlandschoot, P., Jou, W. M., and Fiers, W., Nat. Med., 5, 1157–1163 (1999).
Neumann, G., Zobel, A. and Hobom, G., Virology, 202, 477–479 (1994).
Neumann, G., Castrucci, M. R. and Kawaoka, Y., J. Virol., 21, 9690–9700 (1997).
Neumann, G., Watanabe, T., Ito, H., Watanabe, S., Goto, H., Gao, P., Hughes, M., Perez, D. R., Donis, R., Hoffmann, E., Hobom, G., and Kawaoka, Y., Proc. Natl. Acad., Sci. USA, 96, 9345–9350 (1999).
Niwa, H., Yamamura, K. and Miyazaki, J., Gene, 108, 193–200 (1991).
Ochman, H., Gerber, A. S., and Hartl, D. L., Genetics, 120, 621–623 (1988).
Ohuchi, M., Cramer, A., Vey, M., Ohuchi, R., Garten, W., and Klenk, H.- D., J. Virol., 68, 920–926 (1994).
Perez, D. R. and Donis, R. O., Virology, 249, 52–61 (1998).
Piller, S. C., Ewart, G. D., Premakumar, A., Cox, G. B., and Gage, P. W., Proc. Natl. Acad. Sci. USA, 93, 111–115 (1996).
Pinto, L. H., Holsinger, L. J., and Lamb, R. A., Cell, 69, 517–528 (1992).
Pleschka, S., Jaskunas, S. R., Engelhardt, O. G., Zurcher, T., Palese, P. and Garcia-Sastre, A., J. Virol., 70, 4188–4192 (1996).
Roizman, B., and Palese, P., In Fields, B. N., Knipe, D. M., and Howley, P. M. (eds) Fields Virology, 3rd ed. Lippincott-Raven Publishers, Philadelphia, Pa., pp. 101–111 (1996).
Sansom, M. S. P., and Kerr, I. D., Protein Eng., 6, 65–74 (1993).
Schubert, U., Clouse, K. A., and Strebel, K., J. Virol., 69, 7699–7711 (1995).
Schnell, M. J., Mebatsion, T., and Conzelmann, K. K. EMBO J. 1, 4195–4203 (1994).
Schubert, U., Ferrer-Montiel, A. V., Oblatt-Montal, M., Henklein, P., Strebel, K., and Montal, M., FEBS Lett., 398, 12–18 (1996).
Sears, S. D., Clements, M. L., Betts, R. F., Maassab, H. F., Murphy, B. R., and Snyder, M. H., J. Infect. Dis., 158, 1209–1219 (1988).
Skehel, J. J., Hay, A. J., and Armstrong, J. A., J. Gen. Virol., 38, 97–110 (1978).
Steinhoff, M. C., Halsey, N. A., Fries, L. F., Wilson, M. H., King, J., Burns, B. A., Samorodin, R. K., Perkis, V., Murphy, B. R., and Clements, M. L., J. Infect. Dis. 163, 1023–1028 (1991).
Steinhoff, M. C., Halsey, N. A., Wilson, M. H., Burns, B. A., Samorodin, R. K., Fries, L. F., Murphy, B. R., and Clements, M. L., J. Infect Dis. 162, 394–401 (1990).
Strebel, K., Klimkait, T. Maldarelli, F., and Martin, M. A., J. Virol, 63, 3784–3791 (1989).
Strebel, K, Klimkait, T., and Martin, M. A., Science 241, 1221–1223 (1988).
Subbarao, E. K., Kawaoka, Y. and Murphy, B. R., J. Virol, 67, 7223–7228 (1993).
Sugrue, R. J., Bahadur, G., Zamborn, M. C., Hall-Smith, M., Douglas, A. R., and Hay, A. J., EMBO J., 9, 3469–3476 (1990).
Sugrue, R. J., and Hay, A. J., Virology 180, 617–624 (1991).
Sunstrom, N. A., Premkumar, L. S., Premkumar, A., Ewart, G., Cox, G. B., and Gage, P. W., J. Membr. Biol., 150, 127–132 (1996).
Takeuchi, K. and Lamb, R. A., J. Virol, 68, 911–919 (1994).
Terwilliger, E. F., cohen, E. A., Lu, Y. C., Sodroski, J. G., and Haseltine, W. A., Proc. Natl. Acad. Sci. USA, 86, 5163–5167 (1989).
Wang, C., Takeuchi, K., Pinto, L. H., and Lamb, R. A., L Virol., 67, 5585–5594 (1993).
Weber, F., Haller, O., and Kochs, G., J. Virol., 70, 8361–8367 (1996).
Weber, F., Haller, O., and Kochs, G., Arch Virol, 142, 1029–1033 (1997).
Wharton, S. A., Calder, L. J., Ruigrok, R. W. H., Skehel, J. J., Steinhauer, D. A., and Wiley, D. C., EMBO J., 14, 240–246 (1995).
Yasuda, J., Bucher, D. J. and Ishihama, A., J. Virol., 68, 8141–8146 (1994).
Zebedee, S. L., and Lamb, R. A., L Virol., 62, 2762–2772 (1988).
Zhirnov, O. P., Virology 1, 274–279 (1990).
Zhirnov, O., and Bukrinskaya, A. G., J. Gen. Virol., 65, 1127–1134 (1984).

All publications, patents and patent applications are incorporated herein by reference. While in the foregoing specification this invention has been described in relation to certain preferred embodiments thereof, and many details have been set forth for purposes of illustration, it will be apparent to those skilled in the art that the invention is susceptible to additional embodiments and that certain of the details described herein may be varied considerably without departing from the basic principles of the invention.

What is claimed is:

1. An isolated and purified recombinant influenza virus comprising a mutant M2 ion channel protein which lacks or has reduced activity relative to the corresponding wild-type M2 ion channel protein, wherein the mutation is in the transmembrane domain of the M2 ion channel protein, wherein the mutation does not substantially alter the in vitro replication of the virus in the absence of amantadine but is associated with attenuation of the virus in vivo, and wherein the mutant M2 ion channel protein lacks one or more residues in the transmembrane domain which include residues 29 to 31.

2. The isolated and purified virus of claim 1 wherein the recombinant virus further comprises a heterologous immunogenic protein of a pathogen.

3. A vaccine comprising the isolated and purified virus of claim 1.

4. A method to immunize a vertebrate, comprising: contacting the vertebrate with an effective amount of the recombinant virus of claim 1.

5. The method of claim 4 wherein the vertebrate is an avian.

6. The method of claim 4 wherein the vertebrate is a mammal.

7. The method of clam 4 wherein the vertebrate is a human.

8. A composition comprising a plurality of influenza vectors, comprising:

a) at least two vectors selected from a vector comprising a promoter operably linked to an influenza virus PA cDNA linked to a transcription termination sequence, a vector comprising a promoter operably linked to an influenza virus PB1 cDNA linked to a transcription termination sequence, a vector comprising a promoter operably linked to an influenza virus PB2 cDNA linked to a transcription termination sequence, a vector comprising a promoter operably linked to an influenza virus HA cDNA linked to a transcription termination sequence, a vector comprising promoter operably linked to an influenza virus NP cDNA linked to a transcription termination sequence, a vector comprising a promoter operably linked to an influenza virus NA cDNA linked to a transcription termination sequence, a vector comprising a promoter operably linked to an influenza virus M cDNA linked to a transcription termination sequence, and a vector comprising a promoter operably linked to an influenza virus NS cDNA linked to a transcription termination sequence, wherein the M cDNA comprises a mutant M2 ion channel protein DNA comprising a mutation in the transmembrane domain of the M2 ion channel protein, wherein the mutant M2 ion channel protein lacks or has reduced activity relative to the corresponding wild-type M2 ion channel protein, wherein the mutation does not substantially alter the in vitro replication of a virus having the mutant M2 ion channel protein in the absence of amantadine but is associated with attenuation of the virus in vivo, wherein the mutant M2 ion channel protein lacks one or more residues in the transmembrane domain which include residues 29 to 31, and wherein one of the selected vectors is the vector comprising the mutant M2 ion channel protein DNA; and b) at least two vectors selected from a vector comprising a promoter operably linked to a DNA segment encoding influenza virus PA, a vector comprising a promoter operably linked to a DNA segment encoding influenza virus PB1, a vector comprising a promoter operably linked to a DNA segment encoding influenza virus PB2, a vector comprising a promoter operably linked to a DNA segment encoding influenza virus NP, a vector comprising a promoter operably linked to a DNA segment encoding influenza virus HA, a vector comprising a promoter operably linked to a DNA segment encoding influenza virus NA, a vector comprising a promoter operably linked to a DNA segment encoding influenza virus M1, a vector comprising a promoter operably linked to a DNA segment encoding an ion channel protein and a vector comprising a promoter operably linked to a DNA segment encoding influenza virus NS2.

9. The composition of claim 8 further comprising a vector comprising a promoter operably linked to a DNA fragment of interest in antisense orientation.

10. The composition of claim 9 wherein the vector comprises a DNA fragment which encodes an immunogenic polypeptide or peptide of a pathogen.

11. An isolated virus prepared by contacting a host cell with a plurality of influenza vectors, wherein the plurality of vectors comprises: a) at least two vectors selected from a vector comprising a promoter operably linked to an influenza virus PA cDNA linked to a transcription termination sequence, a vector comprising a promoter operably linked to an influenza virus PB1 cDNA linked to a transcription termination sequence, a vector comprising a promoter operably linked to an influenza virus PB2 cDNA linked to a transcription termination sequence, a vector comprising a promoter operably linked to an influenza virus HA cDNA linked to a transcription termination sequence, a vector comprising promoter operably linked to an influenza virus NP cDNA linked to a transcription termination sequence, a vector comprising a promoter operably linked to an influenza virus NA cDNA linked to a transcription termination sequence, a vector comprising a promoter operably linked to an influenza virus M cDNA linked to a transcription termination sequence, and a vector comprising a promoter operably linked to an influenza virus NS cDNA linked to a transcription termination sequence, wherein the M cDNA comprises mutant M2 ion channel protein DNA comprising a mutation in the transmembrane domain, wherein the mutant M2 ion channel protein lacks or has reduced activity relative to the corresponding wild-type M2 ion channel protein, wherein the mutation does not substantially alter the in vitro replication of the virus in the absence of amantadine but is associated with attenuation of the virus in viva, wherein the mutant M2 ion channel protein lacks one or more residues in the membrane domain which include residues 29 to 31, and wherein one of the selected vectors is the vector comprising the mutant M2 ion channel protein DNA; and b) at least two vectors selected from a vector comprising a promoter operably linked to a DNA segment encoding influenza virus PA, a vector comprising a promoter operably linked to a DNA segment encoding influenza virus PB1, a vector comprising a promoter operably linked to a DNA segment encoding influenza PB2, a vector comprising a promoter operably linked to a DNA segment encoding influenza virus NP, a vector comprising a promoter operably link ed to a DNA segment encoding influenza virus HA, a vector comprising a promoter operably linked to a DNA segment encoding influenza virus NA, a vector comprising a promoter operably linked to a DNA segment encoding influenza virus M1, a vector comprising a promoter operably linked to a DNA segment encoding an ion channel protein, and a vector comprising a promoter operably linked to a DNA segment encoding influenza virus NS2.

12. An isolated host cell contacted with the virus of claim 1 or 11.

13. The isolated and purified virus of claim 1 wherein the mutation is the deletion of residues 29 to 31 of the transmembrane domain of M2.

14. The isolated and purified virus of claim 1 wherein the mutation provides a selective growth advantage to the recombinant virus in the presence of a concentration of amantadine which inhibits the replication of a corresponding virus which does not comprise the mutant M2 ion channel protein.

15. A method of preparing a recombinant influenza virus comprising a mutant ion channel protein which lacks or has reduced activity relative to the corresponding wild-type ion channel protein, comprising:

(i) contacting a host cell with a plurality of influenza vectors so as to yield recombinant influenza virus, wherein the plurality of vectors comprises: a) at least two vectors selected from a vector comprising a promoter operably linked to an influenza virus PA cDNA linked to a transcription termination sequence, a vector comprising a promoter operably linked to an influenza virus PB 1 cDNA linked to a transcription termination sequence, a vector comprising a promoter operably linked to an influenza virus PB2 cDNA linked to a transcription termination sequence, a vector comprising a promoter operably linked to an influenza virus HA cDNA linked to a transcription termination sequence, a vector comprising promoter operably linked to an influenza virus NP cDNA linked to a transcription termination sequence, a vector comprising a promoter operably linked to an influenza virus NA cDNA linked to a transcription termination sequence, a vector comprising a promoter operably linked to an influenza virus M cDNA linked to a transcription termination sequence, and a vector comprising a promoter operably linked to an influenza virus NS cDNA linked to a transcription termination sequence, wherein the M cDNA comprises mutant M2 ion channel protein DNA which encodes a mutant M2 ion channel protein which lacks or has reduced activity relative to the corresponding wild-type M2 ion channel protein, wherein the mutation is in the transmembrane domain of the M2 ion channel protein, wherein the mutation does not substantially alter the in vitro replication of the virus in the absence of amantadine but is associated with attenuation of the virus in vivo, wherein the mutant M2 ion channel protein lacks one or more residues in the transmembrane domain which include residues 29 to 31, and wherein one of the selected vectors is the vector comprising the mutant M2 ion channel protein DNA; and b) at least two vectors selected from a vector comprising a promoter operably linked to a DNA segment encoding influenza virus PA, a vector a comprising a promoter operably linked to a DNA segment encoding influenza virus PB1, a vector comprising a promoter operably linked to a DNA segment encoding influenza virus PB2, a vector comprising a promoter operably linked to a DNA segment encoding influenza virus NP, a vector comprising a promoter operably linked to a DNA segment encoding influenza virus HA, a vector comprising a promoter operably linked to a DNA segment encoding influenza virus NA, a vector comprising a promoter operably linked to a DNA segment encoding influenza virus M1, a vector comprising a promoter operably linked to a DNA segment encoding an ion channel protein, and a vector comprising a promoter operably linked to a DNA segment-encoding influenza virus NS2; and (ii) isolating the virus.

16. The method of claim 15 wherein the mutation is the deletion of residues 29 to 31 of the transmembrane domain of M2.

17. A virus prepared by the method of claim 15.

* * * * *

UNITED STATES PATENT AND TRADEMARK OFFICE
CERTIFICATE OF CORRECTION

PATENT NO. : 6,872,395 B2
DATED : March 29, 2005
INVENTOR(S) : Kawaoka

It is certified that error appears in the above-identified patent and that said Letters Patent is hereby corrected as shown below:

Title page,
Item [56], References Cited, OTHER PUBLICATIONS, "Duff, K.C. et al.," reference, delete "Vilology" and insert -- Virology --, therefor.
"Pleschka, S., et al., delete "Gentics" and insert -- Genetics --, therefor.

Column 37,
Line 20, after "protein" insert -- , --.
Line 56, delete "viva" and insert -- vivo --, therefor.
Line 66, after "influenza" insert -- virus --.

Column 38,
Line 2, delete "link ed" and insert -- linked --, therefor.
Line 66, after "vector" delete "a".

Column 40,
Line 3, delete "segment-encoding" and insert -- segment encoding --, therefor.

Signed and Sealed this

Twelfth Day of July, 2005

JON W. DUDAS
*Director of the United States Patent and Trademark Office*